(12) United States Patent
Kemp et al.

US008114670B2

(10) Patent No.: US 8,114,670 B2
(45) Date of Patent: Feb. 14, 2012

(54) SKIN EQUIVALENT CULTURE

(75) Inventors: Paul Kemp, Manchester (GB); David Shering, Manchester (GB); Andrew Shering, legal representative, Manchester (GB); Penny Johnson, Manchester (GB); Damian Marshall, Manchester (GB)

(73) Assignee: DFB Technology Holdings, LLC, Fort Worth, TX (US)

( * ) Notice: Subject to any disclaimer, the term of this patent is extended or adjusted under 35 U.S.C. 154(b) by 812 days.

(21) Appl. No.: 11/886,113

(22) PCT Filed: Mar. 14, 2006

(86) PCT No.: PCT/GB2006/000890
§ 371 (c)(1),
(2), (4) Date: Jun. 24, 2008

(87) PCT Pub. No.: WO2006/097701
PCT Pub. Date: Sep. 21, 2006

(65) Prior Publication Data
US 2010/0203135 A1 Aug. 12, 2010

(30) Foreign Application Priority Data
Mar. 14, 2005 (GB) .................................. 0505202.2

(51) Int. Cl.
*C12N 5/00* (2006.01)
*G01N 33/53* (2006.01)
*A01N 63/00* (2006.01)
*A61K 9/14* (2006.01)

(52) U.S. Cl. ........ 435/395; 424/93.7; 424/484; 435/7.1; 435/383

(58) Field of Classification Search ........................ None
See application file for complete search history.

(56) References Cited

U.S. PATENT DOCUMENTS

| 5,591,444 | A | 1/1997 | Boss, Jr. |
| 5,858,390 | A | 1/1999 | Boss, Jr. |
| 6,124,522 | A | 9/2000 | Schroeder |
| 6,533,819 | B1 | 3/2003 | Urry et al. |
| 6,596,304 | B1 * | 7/2003 | Bayon et al. ................. 424/444 |
| 6,699,470 | B1 | 3/2004 | Ameer et al. |
| 6,878,383 | B2 | 4/2005 | Boss, Jr. et al. |
| 2002/0161440 | A1 | 10/2002 | Son et al. |
| 2003/0069639 | A1 | 4/2003 | Sander et al. |
| 2003/0165482 | A1 | 9/2003 | Rolland et al. |
| 2004/0029095 | A1 | 2/2004 | Lowel et al. |
| 2004/0082063 | A1 | 4/2004 | Deshpande et al. |
| 2004/0162615 | A1 | 8/2004 | Lam et al. |

FOREIGN PATENT DOCUMENTS

| DE | 4127570 | 2/1993 |
| DE | 10116362 | 10/2002 |
| EP | 0242305 | 10/1987 |
| EP | 0344924 | 12/1989 |
| EP | 1184040 | 3/2002 |
| EP | 0989866 | 9/2002 |
| EP | 1358857 | 11/2003 |
| EP | 1375647 | 1/2004 |
| EP | 1137380 | 3/2004 |
| RU | 2023424 | 11/1994 |
| RU | 2195889 | 1/2003 |
| RU | 2273457 | 4/2006 |
| WO | WO 98/36704 | 8/1998 |
| WO | WO 99/15637 | 4/1999 |
| WO | WO 99/51164 | 10/1999 |
| WO | WO 01/32129 | 5/2001 |
| WO | WO 02/072113 | 9/2002 |
| WO | WO 03/041568 | 5/2003 |
| WO | WO 03/084385 | 10/2003 |

OTHER PUBLICATIONS

Neidert et al., "Enhanced Fibrin Remodeling In Vitro with TGF-I~I, Insulin and Plasmin for Improved Tissue-Equivalents," Biomaterials 23:3717-3731,2002.*
Park et al. Biomaterials 24:1631-1641, 2003.*
Geesin et al., "Regulation of Collagen Synthesis in Human Dermal Fibroblasts in Contracted Collagen Gels by Ascorbic Acid, Growth Factors, and Inhibitors of Lipid Peroxidation," *Exp. Cell Res.* 206:283-290, 1993.
Hansbrough et al., "Composite Grafts of Human Keratinocytes Grown on a Polyglactin Mesh-Cultured Fibroblast Dermal Substitute Function as a Bilayer Skin Replacement in Full-Thickness Wounds on Athymic Mice," *J. Burn Care & Rehab.* 14:485-494, 1993. Meana et al., "Large Surface of Cultured Human Epithelium Obtained on a Dermal Matrix Based on Live Fibroblast-Containing Fibrin Gels," *Burns* 24:621-630, 1998.
Neidert et al., "Enhanced Fibrin Remodeling In Vitro with TGF-β1, Insulin and Plasmin for Improved Tissue-Equivalents," *Biomaterials* 23:3717-3731, 2002.
Office Communication, issued in Australian Patent Application No. 2006224355, dated Nov. 10, 2010.
Berfield et al., "Insulin-Like Growth Factor I (IGF-I) Induces Unique Effects in the Cytoskeleton of Cultured Rat Glomerulat Mesangial Cells," *J. Histochem. & Cytochem.* 45:583-593, 1997.

(Continued)

*Primary Examiner* — Janet L Epps-Smith
(74) *Attorney, Agent, or Firm* — Fulbright & Jaworski L.L.P.

(57) ABSTRACT

Methods of forming soft connective tissue compositions such as skin equivalents, compositions made by the methods and their uses. In particular, a method of forming a connective tissue equivalent, comprising the steps of: (i) incubating collagen-producing cells in or on a support matrix; (ii) inducing and/or enhancing collagen production by the collagen-producing cells to form a collagenous construct and degradation and replacement of the support matrix; (iii) freeze-drying the construct; and (iv) re-populating the freeze-dried construct with collagen-producing cells and/or epithelial cells and/or endothelial cells and/or mesenchymal cells, thereby forming a connective tissue equivalent, wherein: (a) the collagen-producing cells are substantially fibroblasts; for example human neonatal dermal fibroblasts; (b) the support matrix is a provisional support matrix in which the support matrix is a fibrin matrix, for example formed by thrombin-mediated polymerisation of fibrinogen; and (c) as a result of the collagen production by the collagen-producing cells the provisional fibrin support matrix is digested by the cells and is replaced by collagen, thereby essentially replacing the provisional fibrin matrix with a collagen matrix synthesised in situ by the cells.

17 Claims, 14 Drawing Sheets

OTHER PUBLICATIONS

Brown et al., "Fibroblast Migration in Fibrin Gel Matrices," *Am. J. Path.* 142:273-283, 1993.

Clark, "Regulation of Fibroplasia in Cutaneous Wound Repair," *Am. J. Med. Sci.* 306:42-48, 1993.

Cullen et al., "The Differential Regulation and Secretion of Proteinases from Fetal and Neonatal Fibroblasts by Growth Factors," *Int. J. Biochem. Cell Biol.* 29:241-250, 1997.

Eckes et al., "Impaired Wound Healing in Embryonic and Adult Mice Lacking Vimentin," *J. Cell Sci.* 113:2455-2462, 2000.

Kessler et al., "Fibroblasts in Mechanically Stressed Collagen Lattices Assume a "Synthetic" Phenotype," *J. Bio. Chem.* 276:36575-36585, 2001.

Kessler-Becker et al., "Expression of Pro-Inflammatory Markers by Human Dermal Fibroblasts in a Three-Dimensional Culture Model is Mediated by an Autocrine Interleukin-1 Loop," *Biochem. J.* 379:351-358, 2004.

Muhart et al., "Behavior of Tissue-Engineered Skin. A Comparison of a Living Skin Equivalent, Autograft, and Occlusive Dressing in Human Donor Sites," *Arch. Dermatol.* 135:913-918, 1999.

Neidert et al., "Fibrin as an Alternative Biopolymer to Type I Collagen for Tissue-Equivalent Fabrication," *BED* 50:215-216, 2001.

Schäffer et al., "Nitric Oxide, an Autocrine Regulator of Wound Fibroblast Synthetic Function," *J. Immunol.* 158:2375-2381, 1997.

Tuan et al., "In Vitro Fibroplasia: Matrix Contraction, Cell Growth, and Collagen Production of Fibroblasts Cultured in Fibrin Gels," *Exp. Cell Res.* 223:127-134, 1996.

Whiteside et al., "Heterogeneous Synthetic Phenotype of Cloned Scleroderma Fibroblasts May be Due to Aberrant Regulation in the Synthesis of Connective Tissues," *Arth. Rheum.* 31:1221-1229, 1988.

Office Communication, issued in Australian Patent Application No. 2011200128, dated May 23, 2011.

* cited by examiner

Figure 5.

| Day 0 | | Day 7 | | Day 14 | | Day 21 | |
|---|---|---|---|---|---|---|---|
| DMEM medium | → severe contraction | | | Study discontinued | | | |
| Total medium | | Total medium | → minimal contraction | | | | |
| DMEM medium | → severe contraction | | | | 56-63 days → | Total medium | minimal contraction |
| DMEM medium | → | Total medium | severe contraction | Study discontinued | | | |
| DMEM medium | → | Total medium +phenytoin | minimal contraction | | 56-63 days → | | |
| Construct cast onto freeze-dried construct + DMEM medium | → | Total medium | minimal contraction | Total medium | minimal contraction | 56-63 days → | |
| 72h serum-free then into DMEM medium | → | Total medium | minimal contraction | | 56-63 days → | | |

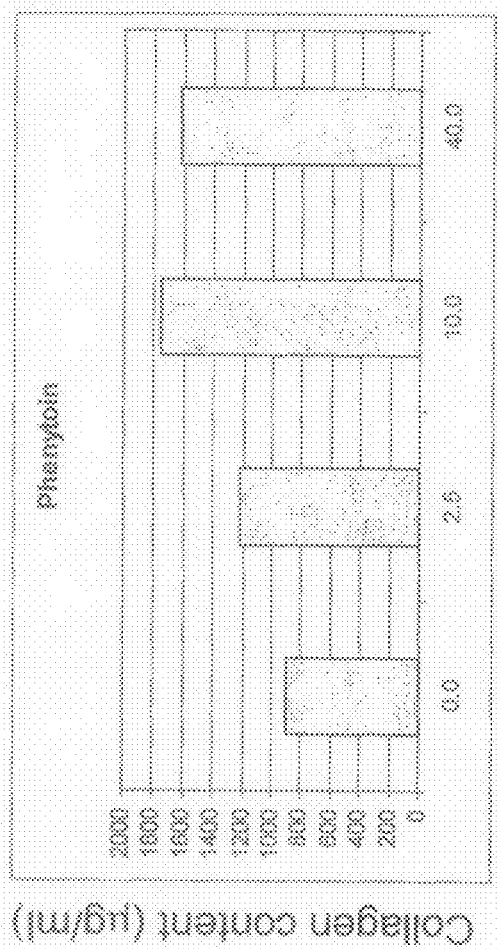
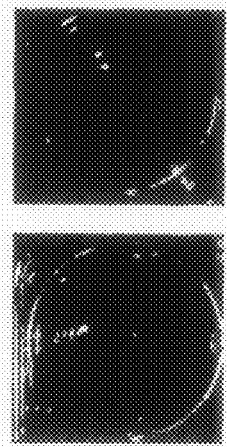
Figure 7.

SKIN EQUIVALENT CULTURE

CROSS-REFERENCE TO RELATED APPLICATIONS

This application is the U.S. National Stage of International Application No. PCT/GB2006/000890, filed on Mar. 14, 2006, which claims the benefit of Great Britain Patent Application No. 0505202.2, filed on Mar. 14, 2005.

The present invention relates to methods of forming soft connective tissue compositions such as skin equivalents, compositions made by the methods and their uses.

Bioengineered skin substitutes have emerged over the past two decades, with the initial intention to replace autograft, allograft, and xenograft in burn applications. Examples of engineered skin substitute products available or anticipated in the market are shown in Table 1. Several of these products are formed from collagen that has been assembled in vitro and seeded with autologous or allogeneic human dermal fibroblasts (HDFs).

TABLE 1

Examples of prior art engineered skin substitute products

| Product | Manufacturer | Composition | Indication |
|---|---|---|---|
| Dermagraft | Smith & Nephew | HDFs seeded into bioabsorbable scaffold (PLA/PGA) Living | Venous, pressure, diabetic foot ulcers |
| TransCyte | Smith & Nephew | HDFs + assembled porcine dermal collagen on nylon mesh + epidermal substitute (silicone) Non-living Temporary covering | Burns |
| ApliGraf | Organogenesis | Assembled bovine tendon collagen + allogeneic HDFs + keratinocytes Living Semi-Permanent | Venous, pressure, diabetic foot ulcers |
| OrCel | Ortec | Assembled bovine collagen sponge + allogeneic HDFs and keratinocytes + non-porous gel Living Semi-Permanent (biodegradable | EB Burns (donor site) |
| Epicel | Genzyme | Autologous human keratinocytes + petrolatum gauze | Burns |

Such skin substitutes have found wide application in the active treatment of chronic venous and chronic diabetic ulcers in particular, but have been shown in practice not to persist on the wound so are not true "skin equivalents". While autologous tissue transfers can be very effective in securing wound healing, such procedures are invasive, painful, and expensive, and cannot be performed by many wound care practitioners. In practical terms, skin equivalents ideally represent artificial, off-the-shelf alternatives to skin grafts that avoid the pain and potential complications of harvesting, are always available in any quantity needed, and can be applied in an office setting.

An ideal skin equivalent would adhere quickly to a skin lesion such as a wound, and once applied would persist, mimicking the physiology and some of the mechanics of normal skin. Furthermore, it would not be subject to immune rejection by the host, and would be highly effective in accelerating tissue regeneration and wound repair rather than accelerating wound healing by secondary intent. Unfortunately, this ideal skin equivalent has not yet been achieved.

Various studies have attempted to provide an in vitro model of fibroplasia, i.e. the process of tissue repair involving extracellular matrix (ECM) reorganisation, cell growth and collagen synthesis or deposition during tissue repair, in order to understand the complex mechanisms underlying the process. Tuan et al. (1996, Exp. Cell Res. 223: 127-134) have provided a fibrin gel culture system in which fibrin gels containing human dermal fibroblasts are stabilised on plastic culture plates as hemispheres. The fibroblasts were able to reorganise and remodel the fibrin matrix, and began the process of synthesising collagen to form a collagen-containing scar-like tissue. Neidert et al. (2002, Biomaterials 23: 3717-3731), using a similar system to Tuan et al. (1996), have demonstrated that fibroblasts seeded into a collagen matrix (as in several of the skin equivalent products shown in Table 1) produce less collagen and extracellular matrix (ECM) than fibroblasts in fibrin. In a related study, Grassl et al. (2002, J. Biomed. Mater. Res. 60: 607-612) examined the use of fibrin as an alternative to collagen for the entrapment of neonatal aortic rat smooth muscle cells in the fabrication of media equivalents. While such studies have furthered our understanding of fibroplasia, there remains a need for improved connective tissue products.

It is also known from the prior art that many factors including ascorbic acid, TGF-β, platelet-derived growth factor (PDGF), epidermal growth factor (EGF), L-proline, insulin and insulin-like growth factor, plasmin, fibrin, phenytoin, valproic acid, cyclosporin A, nifedipine, diltiazem, verapamil HCl and amolldipine and mechanical stress influence collagen formation by cells such as fibroblasts. For example, WO02/49603 discloses a topical composition for prevention and alleviation of wrinkling which comprises one or two or more selected from the group consisting of phenytoin, valproic acid, cyclosporin A, nifedipine, diltiazem, verapamil HCl and amolldipine as an active ingredient having an effect of boosting collagen synthesis when applied to a skin surface comprising fibroblasts. However, optimal combinations of such factors, together with other variables such as concomitant stimulation by physical stress and selection of a medium feeding regime, have not been determined for tissue engineered applications.

The present inventors have developed an alternative method for forming a connective tissue construct which offers improvements over prior art methods and constructs.

According to a first aspect of the present invention, there is provided a method of forming a connective tissue equivalent, comprising the steps of:
(i) incubating collagen-producing cells in or on a support matrix;
(ii) inducing and/or enhancing collagen production by the collagen-producing cells to form a collagenous construct;
(iii) freeze-drying the construct; and
(iv) re-populating or seeding the freeze-dried construct with collagen-producing cells and/or epithelial cells and/or endothelial cells and/or mesenchymal cells, thereby forming a connective tissue equivalent.

In particular the invention provides a method of forming a connective tissue equivalent, comprising the steps of:
(i) incubating collagen-producing cells in or on a support matrix;
(ii) inducing and/or enhancing collagen production by the collagen-producing cells to form a collagenous construct;
(iii) freeze-drying the construct; and
(iv) re-populating the freeze-dried construct with collagen-producing cells and/or epithelial cells and/or endothelial cells and/or mesenchymal cells, thereby forming a connective tissue equivalent, wherein:

(a) the collagen-producing cells are substantially fibroblasts; for example human neonatal dermal fibroblasts;
(b) the support matrix is a provisional support matrix in which the support matrix is a fibrin matrix, for example formed by thrombin-mediated polymerisation of fibrinogen; and
(c) as a result of the collagen production by the collagen-producing cells the provisional fibrin support matrix is digested by the cells and is replaced by collagen, thereby essentially replacing the provisional fibrin matrix with a collagen matrix synthesised in situ by the cells.

The method steps combine and can be manipulated as described herein to form a connective tissue equivalent with appropriate properties such as strength, rigidity, elasticity and/or flexibility, which properties can be varied according to the desired characteristics of the tissue equivalent.

The collagenous construct may be defined as a construct having a non-cellular component containing at least 10% to 99% collagen.

The freeze-dried construct may be re-populated or seeded with epidermal keratinocytes, for example, and allowing cornification to occur, so as to provide further strength and rigidity to the connective tissue equivalent.

Collagen production may be induced and/or enhanced by chemical means and/or mechanical means. The chemical means may comprise a collagen-inducing medium (which term encompasses a medium which may additionally or alternative enhance collagen production).

The collagen-inducing medium may comprise one or more of the group consisting of phenytoin, ascorbic acid, valproic acid, cyclosporin A, nifedipine, diltiazem, verapamil HCl and amolldipine.

Additionally or alternatively, the collagen-inducing medium may comprise one or more of the group consisting of Dulbecco's Modified Eagle's Medium (DMEM), Hams F-12 medium, newborn calf serum and/or fetal calf serum, L-glutamine, epidermal growth factor, hydrocortisone, ethanolamine, o-phosphoryl-ethanolamine, transferrin, triiodothyronine, selenium, L-proline and glycine. A "Total medium" comprising these components has been shown to be particularly effective at inducing collagen formation in the connective tissue construct.

The collagen-inducing medium may further comprise one or more of the group consisting of insulin, epidermal growth factor (EGF), TGF-β, polyethylene glycol (PEG), platelet-derived growth factor (PDGF) and plasmin.

Components of the collagen-inducing medium may also be varied to increase the amount of elastin produced by the collagen-producing cells.

The collagen-inducing medium may be changed daily, up to 5 times a week, for example 3 times a week, weekly or fortnightly, optionally with different frequency of changes during formation of the collagenous construct. The inventors have found that if collagen-inducing medium is changed three times a week, compared with daily changes, then higher levels of collagen and lower levels of elastin are produced. The required medium changing or feeding regime may thus be varied according to the desired strength and rigidity of the connective tissue equivalent. A combination of different feeding regimes may be desirable, such as initially changing collagen-inducing medium over a longer period followed by more frequent changes, or vice versa. For example, collagen-inducing medium may be changed only once in a first week followed by three changes per week for the remainder of the period of formation of the collagenous construct.

Additionally or alternatively, the collagen-producing cells may be incubated in a proliferating medium before or during incubation in or on the support matrix. The proliferating medium allows the collagen-producing cells to reach a suitable number or stage of proliferation or development. The proliferating medium may comprise one or more of the group consisting of Dulbecco's Modified Eagle's Medium (DMEM), newborn calf serum, fetal calf serum and L-glutamine.

The collagen-producing cells may be incubated in the proliferating medium for a period of 0 to 21 days, preferably up to 7 or 14 days.

The method may comprise a further step of culturing the collagen-producing cells in a serum-free medium before or during incubation in or on the support matrix. For example, the collagen-producing cells may be cultured in the serum-free medium for a period of 0 to 7 days, for example up to 2 or 3 days.

Additionally or alternatively cycles of incubation in serum-free and collagen-forming medium may be repeated continuously throughout the formation of the collagen-forming construct.

The preferred total incubation and induction of collagen production times are: a minimum of 21 days and a maximum of 63 days: most preferable would be 21-49 days or 21-35 days or 21-29 days.

In a preferred embodiment, the collagen-producing cells are substantially fibroblasts, for example 90% to 100%, preferably 95% to 99.5%, and more preferably 97.5% to 99% fibroblasts. The fibroblasts may be dermal fibroblasts, preferably human dermal fibroblasts. A preferred embodiment comprises allogeneic human foreskin-derived fibroblasts.

The support matrix may be a provisional support matrix, for example a matrix which disintegrates or dissolves as the collagenous construct is formed or when the construct is freeze-dried.

The support matrix may be a fibrin matrix, for example formed by thrombin-mediated polymerisation of fibrinogen.

A preferred connective tissue equivalent is based on casting human dermal fibroblasts (HDFs) in fibrin gels. Previous work by groups such as Tuan et al. (1996) and Neidert et al. (2002) has demonstrated that in similar compositions, HDFs are induced to lay down collagen and other extra-cellular matrix materials and, as the construct matures, the original fibrin is replaced by collagen that becomes or can be induced to become cross-linked. Collagen produced by allogeneic HDFs embedded initially in the fibrin gel, would be auto-synthesised and thus more likely to resemble collagen laid down in an authentic wound healing process, for example.

The support matrix may be cast onto a base surface. This base surface may be a form, for example, and could be used for latter application and/or manipulation of the connective tissue construct (for example during therapy).

The base surface may be a freeze-construct construct as defined herein. The advantages of such a base surface are described below.

In one aspect, the connective tissue equivalent is formed using two or more stacked freeze-dried constructs. At least two of the two or more freeze-dried constructs may be separated by an interlaying substance. The interlaying substance may comprise fibrin. The interlaying substance may for example provide rigidity to the tissue equivalent.

The connective tissue equivalent may be a replacement heart valve or a blood valve. In a preferred aspect of the invention, the connective tissue equivalent is a skin equivalent.

The skin equivalent in a preferred embodiment comprising HDFs in a fibrin gel differs from prior art products such as ApliGraf (see Table 1) because, for example, collagen produced by allogeneic HDFs embedded initially in the fibrin gel, would be auto-synthesised and thus more likely to resemble collagen laid down in the authentic wound healing process.

The connective tissue equivalent preferably has at least one, for example at least two, three or all, substantially linear lateral edges. The equivalent may thus be substantially square or rectangular in plan view. Such geometry allows two or more connective tissue equivalents to be connectable along their lateral edges.

The mechanical means for inducing and/or enhancing collagen production may comprise any one or more of the group consisting of electrical stimulation, tension, movement, ultrasound and infrared light.

In a further aspect of the invention there is provided a connective tissue equivalent formed by the method as described herein. The connective tissue equivalent is preferably a skin equivalent.

There is also provided according to the invention the use of the skin equivalent as described herein in the manufacture of a medicament for the treatment of a skin lesion.

Additionally there is provided a method of treating a patient suffering from a skin lesion comprising topically applying a skin equivalent as defined hereinto the skin lesion.

The skin lesion suitable for treatment by the skin equivalent includes a venous ulcer, diabetic ulcer, pressure sore, burn or iatrogenic grating wound.

In another aspect of the invention there is provided a collagen-inducing medium as defined herein, for example "Total medium" (in particular the specific ingredients as defined below).

Various groups have used medias and components to stimulate collagen synthesis. For example, Organogenesis (US application 20020172705) used the following medium:
a base 3:1 mixture of DMEM: Hams F-12 medium (Quality Biologics, US),
4 mM GlutaMAX (Gibco),
5 ng/ml human recombinant epidermal growth factor (Upstate Biotechnology, US),
0.4 mg/ml hydrocortisone (Sigma),
$1 \times 10^{-4}$ M ethanolamine (Fluka),
$1 \times 10^{-4}$ M o-phosphoryl-ethanolamine (Sigma),
5 mg/ml insulin (Sigma),
5 mg/ml transferrin (Sigma),
20 pM triiodothyronine (Sigma),
6.78 ng/ml selenium (Sigma),
50 ng/ml L-ascorbic acid (WAKO Chemicals, US),
0.2 µg/ml L-proline (Sigma),
0.1 mg/ml glycine (Sigma), and
0.05% poly-ethylene glycol (PEG) (Sigma).

Neidert et al (2002) used M199 (Gibco) medium supplemented with the following ingredients:
50 U/ml penicillin,
50 µg/ml streptomycin,
1% fungizone (Gibco)
2 mM L-glutamine,
10% FBS, and
50 mg/ml ascorbate (Sigma),
optionally including an additional 10% FBS, 5 ng/ml active TGF-β1 (R&D Systems), 2 µg/ml insulin (sigma( and/or 0.01 U plasmin (Calbiochem) per ml (fibrin).

In one aspect of the present invention, the collagen-inducing medium comprises the combined ingredients of the Organogenesis (US application 20020172705) and Neidert et al. (2002) media, preferably without duplication of common ingredients, optionally combined with phenytoin and/or PDGF and/or VEGF.

Discussion of Prior Art and the Present Invention
D1—Hansbrough J F, Morgan J L, Greenleaf G E and Bartel R. (1993). Composite grafts of Human keratinocytes grown on a polyglactin mesh-cultured fibroblast dermal substitute function as a bilayer skin replacement in full-thickness wounds on athymic mice. *J. Burn Care and Rehab.* 14 (5), 485-494.
D2—Geesin et al, Regulation of Collagen Synthesis in human dermal fibroblsts in contracted collagen gels by ascorbic acod, growth factors, and inhibitors of lipid peroxidation. Experimental Cell Research 206, 283-290.
D3—WO 03/41568 (University of New Jersey, Hewitt et. al) A Three dimensional matrix for producing living tissue equivalents.

Overview of ICX-SKN—Skin Equivalent Culture, According to the Invention:

ICX-SKN has been designed as an active cell therapy consisting of human dermal fibroblasts (HDFs) embedded in fibrin gels which are allowed to mature over several weeks. A key aspect of this maturation period is that under such conditions the original fibrin gel is gradually replaced or substantially augmented by collagen and other components of the extracellular matrix (ECM) leading to a product that is ultimately composed of extracellular matrix auto-manufactured by HDFs.

Following maturation, ICX-SKN can be treated in a number of ways:
  Packaged in transport media (dernis only)
  Populate with Keratinocytes prior to packing
  Freeze-dried and packaged (and potentially stored for up to 18 months)
  Freeze dried and re-populated with cells for shipment (or matured after repopulation)

Applying epidermal keratinocytes to the collagen construct and allowing cornification to occur in situ could provide further strength, rigidity, and function particularly in large area defects.

ICX-SKN can be distinguished from other available products on the basis that the collagen produced by allogeneic HDFs is auto-synthesized by the HDFs and thus more likely to resemble collagen laid down in the authentic wound healing/closure process. The intended application of ICX-SKN can be distinguished from other currently available products, in that being equivalent to a skin graft, ICX-SKN would not heal by secondary intent upon breakdown of the product in situ. Nor is ICX-SKN intended as a temporary covering on the wound. In effect, ICX-SKN is intended to be a wound closure therapy that would act like a skin graft and which we envisage would have a similar life-long effect.

Fibrin Matrix

The present invention relates to methods for forming a skin equivalent that heals by primary intent. Unlike other skin equivalents, the end product described herein is effectively auto-synthesised from the cells which are cast into a provisional scaffold (fibrin) during at an early stage during the manufacturing process.

The provisional fibrin matrix into which cells are cast serves three aims:
1. Fibrin serves as a provisional scaffold that allows three dimensional distribution of HDFs within the constructs which is physiologically relevant to the authentic dermal wound healing environment which provides structure and alignment to cells and fibers.
2. Fibrin provides cues that stimulate cells to deposit collagen forming a more permanent and persistent matrix.
3. The method of casting the fibrin cast as described herein provides mechanical constraint and tension which is also a stimulant of collagen deposition by cells and aids correct alignment of cells and fibers.

The provisional fibrin scaffold can be sufficiently remodeled by newly formed collagen fibers during the period of maturation in collagen boosting medium.

Summary of D1

Hansbrough et al, have developed a "skin replacement" product by combining human epidermal keratinocytes with the commercially available product Dermagraft. Dermagraft is a bioabsorbable polyglactin-910 (Vicryl) scaffold seeded with human dermal fibroblasts which are subsequently matured for 2-3 weeks before being cryopreserved. During the maturation process the fibroblasts differentiate and produce extracellular matrix proteins, which are secreted into the scaffold.

Hansbrough seeded human neonatal foreskin onto a surgical mesh composed of polyglactin-910. The cells were allowed to proliferate and become confluent over a maturation period of 2-3 weeks, after which they were cryopreserved at −70° C. in DMEM-20% FBS-10% DMSO. To make their skin equivalent Hansbrough et al have thawed a piece of Dermagraft and seeded $1.4 \times 10^8$ cell per 100 cm$^2$ and allowed the epidermal cells to become confluent over a 4-6 day culture period. After this culture period the skin equivalents were transplanted onto athymic mice which had a piece of 2×2 cm full thickness skin removed from the dorsolateral surface. The animals were examined after 10 and 20 days post-transplantation by light microscopy and immunohistochemistry.

The authors also suggest that keratinocyte seeded Dermagraft offers advantages in terms on handle-ability and ability to be stapled/sutured into place. Furthermore, the authors suggest that Dermagraft brings about healing by supporting ingress of epithelial cells to the interstices of the mesh rather than by closure of the wound per se.

Pre-Formed Synthetic Network

Dermagraft is formed by seeding human dermal fibroblasts (HDFs) and, in this publication, human keratinocytes (HKs), onto a polyglactin-910 surgical mesh. Over time, the mesh is resorbed into the body. The object of our invention requires that, prior to placement in the wound, a substantial matrix is synthesised by the fibroblasts themselves. Rather than seeding HDFs into a preformed manufactured substrate, HDFs are seeded into a provisional matrix comprised of fibrin, and matured for 21-63, preferably 49 days. In the process of wound-healing, fibrin is present in the wound and induces fibroblast migration into the wound. Once there, fibroblasts digest fibrin and, in time, replace it with collagen and other components of ECM. In the present invention, this process is replicated in the laboratory and results in a matrix that is produced in a manner that is recognisable as a mirror of the natural process and which takes place prior to placement on the wound. During this incubation period the original fibrin matrix is remodelled and infiltrated by collagen deposition laid down by fibroblasts. At time of grafting the original matrix has been infiltrated by autosynthesized collagen and the product is substantially cell-made.

Dermagraft is Cryopreserved.

The process of manufacture of the products of the prior art presents a scenario whereby the final product (with our without keratinocytes) is preserved in a cryoprotective solution in which it is packaged and presented to the end-user.

The object of the present invention is freeze-dried at the point in manufacture where the product in the prior art would be cryopreserved. However, rather than presenting the freeze-dried product of our invention as the final manufactured product, it is rendered through the process of freeze-drying and subsequent sterilisation as a raw material in our final manufacturing process. During the freeze-drying/sterilisation steps, the HDFs originally present in the product of our invention are killed. Having gone through this process, the product of our invention can be held in inventory. In the final phase of manufacture, which can be completed at our discretion as and when stocks are required, the freeze-dried/sterilised product is re-seeded with fibroblasts (with or without keratinocytes), matured (e.g. for a maximum of five days), then shipped in shipping medium to the final end user. In consequence, our product is ready to use by the end user and does not require further processing to rid the product of cryopreservative solution.

Healing by Secondary Intent

In the Introduction the authors of D1 state that "Initial studies demonstrated that Dermagraft could vascularize beneath meshed skin grafts used to close full-thickness wounds in animals and in humans and to support epithelial closure of the mesh graft interstices". The view of the authors themselves is that Dermagraft brings about healing by supporting ingress of epithelial cells to the interstices of the mesh rather than by closure of the wound per se. The object of the invention we describe is to bring about wound closure, with or without applied keratinocytes, rather than to stimulate wound healing. The novelty of the invention is to heal by first intent.

Summary of D2

Geesin et. al. have examined whether the presence of a collagen matrix influences the responses of dermal fibroblasts to ascorbic acid. In brief, the authors mixed fibroblasts and collagen, allowed them to contract for 6 days to form a matrix and then examined the concentration and time dependence for ascorbic acid to affect collagen synthesis. The outcome of these experiments was that ascorbic acid does stimulate collagen synthesis in fibroblasts (in a manner similar to that found in mono-layer fibroblasts).

This paper merely highlights the importance of ascorbic acid and it's effect upon collagen synthesis. ICX-SKN does incorporate the use of ascorbic acid in its media. However, unlike the work by Geesin et al, ICX-SKN consists of fibroblasts in a fibrin matrix during the early stages, NOT fibroblasts within a collagen contracted matrix.

Summary of D3

WO 03/41568 is directed to a 3-d matrix, a living tissue equivalent and methods of making thereof. The 3d matrix comprises blood plasma, thrombin and fibroblasts. Human fibroblasts were suspended in a solution of plasma, and placed in 12 well culture plates. Thrombin solution was added to each well, resulting in the formation of a 3d matrix. Cultures were grown in standard fibroblast culture media to for 10 days with media changes everyday. Following the 10 day culture period HKs were plated on top of the matrixes and a number of supplemented media changes undertaken. Immunohistochemical analysis was undertaken to determine levels of Collagen.

Replacement of Fibrinogen with Collagen

According to the present invention the provisional support matrix is degraded and replaced as the collagenous construct is formed. The connective tissue equivalent is based on casting human dermal fibroblasts (HDFs) in fibrin gels. HDFs are induced to lay down collagen and other extra-cellular matrix materials and, as the construct matures, the original fibrin is replaced by collagen that becomes or can be induced to become cross-linked. The end product of the invention can be effectively fibrin-free, in which the original matrix has been broken down and replaced with collagen.

The disclosure of Hewitt et al, describes the formation of the collagen matrix by "including fibroblasts in a hemostatic clot mixture . . . wherein fibrinogen polymerizes and crosslinks to produce an insoluble fibrin matrix." It is clearly the intention in the invention described by Hewitt et al. that the hemostatic (fibrin) clot should persist in the presence of collagen.

The approach utilized by Hewitt clearly differs from the mechanism in ICX-SKN. In particular, the present application in which the use of TGF-β as a means of inhibiting rapid fibroblast multiplication which thereby prevents destruction of the hemostatic clot. Furthermore, it is embodied in our invention that plasmin can be included in the growth medium of the constructs as plasmin is a specific means of facilitating the breakdown or dissolution of fibrin clots.

Formation of the Fibrin Construct

A key aspect in the casting process of ICX-SKN is that the liquid mixture (fibrinogen, cells+medium, thrombin) does not contact the supporting walls of the vessel into which it is cast since this breaks surface tension and allows the liquid mixture to "creep" up the walls of the vessel. This results in a concave rather than the desired convex shape, and loss in height of the construct. The agitation described in Hewitt et al. (pg 19, [57]) would result in loss of the surface tension that is important in forming the fibrin-construct of our invention and thus would release the "constrained compaction" important in forming tissue engineered constructs of sufficient stiffness and strength.

Maturation and Structure of Collagenous Constructs

In the description of ICX-SKN, we have illustrated examples of incubating constructs intended to form "living skin equivalents" for 49 days to produce a collagen matrix with sufficient structural integrity through the formation of crosslinks between and within collagen molecules in order that it will act substantially as a dermal replacement in a "living skin equivalent". In addition, ascorbic acid, and other ingredients, are added to the growth media in order that the necessary post-translational modifications to the collagen occur within the long maturation period that we describe. Furthermore, we describe the application of physical (mechanical, ultrasound, etc.) stress to our constructs in order to produce yet more collagen and attendant structure to further enhance their properties. Freeze-drying the constructs, as we have described, further adds stability and strength to the constructs of our invention.

The examples described in Hewitt et al, (page 20, [59]) suggest the matrix is only incubated for ten days, followed by the additional step of placing human keratinocytes on top in hopefully form an epidermal layer. Hewitt et al, further state that the addition of Vitmain C Page 13 [42] is optional since it is involved in post-translational modifications to collagen required in forming the "final structure of the collagen molecule". Whilst it is accepted that collagen will be produced in the period of incubation (10 days) as described by Hewitt et al., without the addition of substantial means of synthesizing or obtaining ascorbic acid (vitamin C) it is doubtful that the collagen will obtain its final structure that is crucial to its function in skin, tendon, etc. Furthermore, within the 10 day incubation described in Hewitt et al., it is unlikely that sufficient structure will form in and between collagen fibres for the resulting construct to be useful as a "living skin equivalent".

Final Product of Treatment

The hemostatic clots described in Hewitt et al. are populated with fibroblasts and secondarily by keratinocytes to form a "living skin equivalent" in their invention. It is implied that the products of their invention would form the basis for use as treatment directly.

In contrast, the products of the present invention can be used as treatment once the collagenous matrix has matured, has been freeze-dried (and sterilised), and repopulated with fresh cells, most probably fibroblasts or fibroblasts and keratinocytes. The product of the present invention can be stored as an intermediate freeze-dried collagenous matrix which can be reconstituted as and when desired to form the functional "living skin equivalent" used as a treatment in wound closure.

FIGURES

Further aspects of the invention are described below as well as specific embodiments of the invention by way of example only with reference to the accompanying figures, of which:

FIG. 1 shows examples of fibrin-based constructs. A) a fibrin-based construct cast onto a 13 mm diameter sterilised coverslip (day 0); B) a fibrin based construct cast onto a sterilised 2 cm×2 cm coverslip (day 0); C) Eight fibrin-based constructs cast directly onto tissue culture plastic (day 42) into the wells of an eight-well tissue culture dish; D) a fibrin construct (approx. 2 cm×2 cm) cast directly onto the bottom surface of a 6-well tissue culture dish;

FIG. 2 shows maturation of fibrin-based constructs over 49 days. A) a 2 cm×2 cm fibrin-based construct on day 0 (d0, day of casting); B) on day 17 days post-casting; and again C) on 43 days post-casting. D) a second construct released from constraint on day 17 post-casting; E) the construct in (C) released from constraint on day 43. F) a second d0 construct being manipulated with forceps; and G) day 49 construct being manipulated with forceps;

FIG. 3 illustrates properties of matured constructs. A) macroscopic (left) and microscopic (right) views of paraffin-embedded sections of constructs matured for 49 days post-casting, and stained with Masson's Trichrome which stains collagen (blue). B) A similar construct cast onto a 2 cm×2 cm glass coverslip, matured for 49 days and freeze-dried in situ and C) a construct similar to (B), but removed from the supporting coverslip prior to being freeze-dried. D) The same construct as (C) viewed under magnification and through polarised light;

FIG. 5 depicts medium composition and feeding regime influences contraction of constructs;

Figure 8:
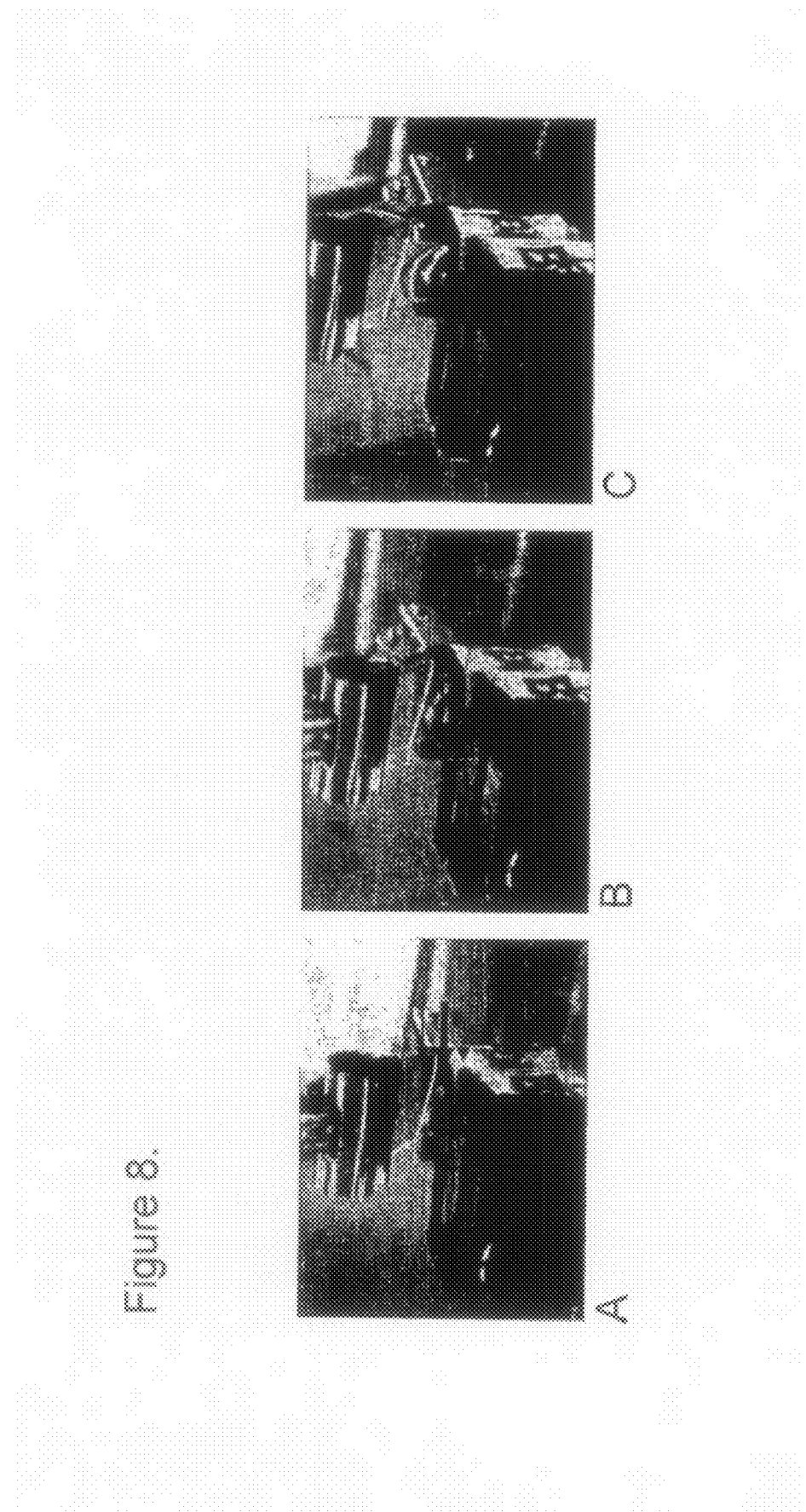
Figure 9:
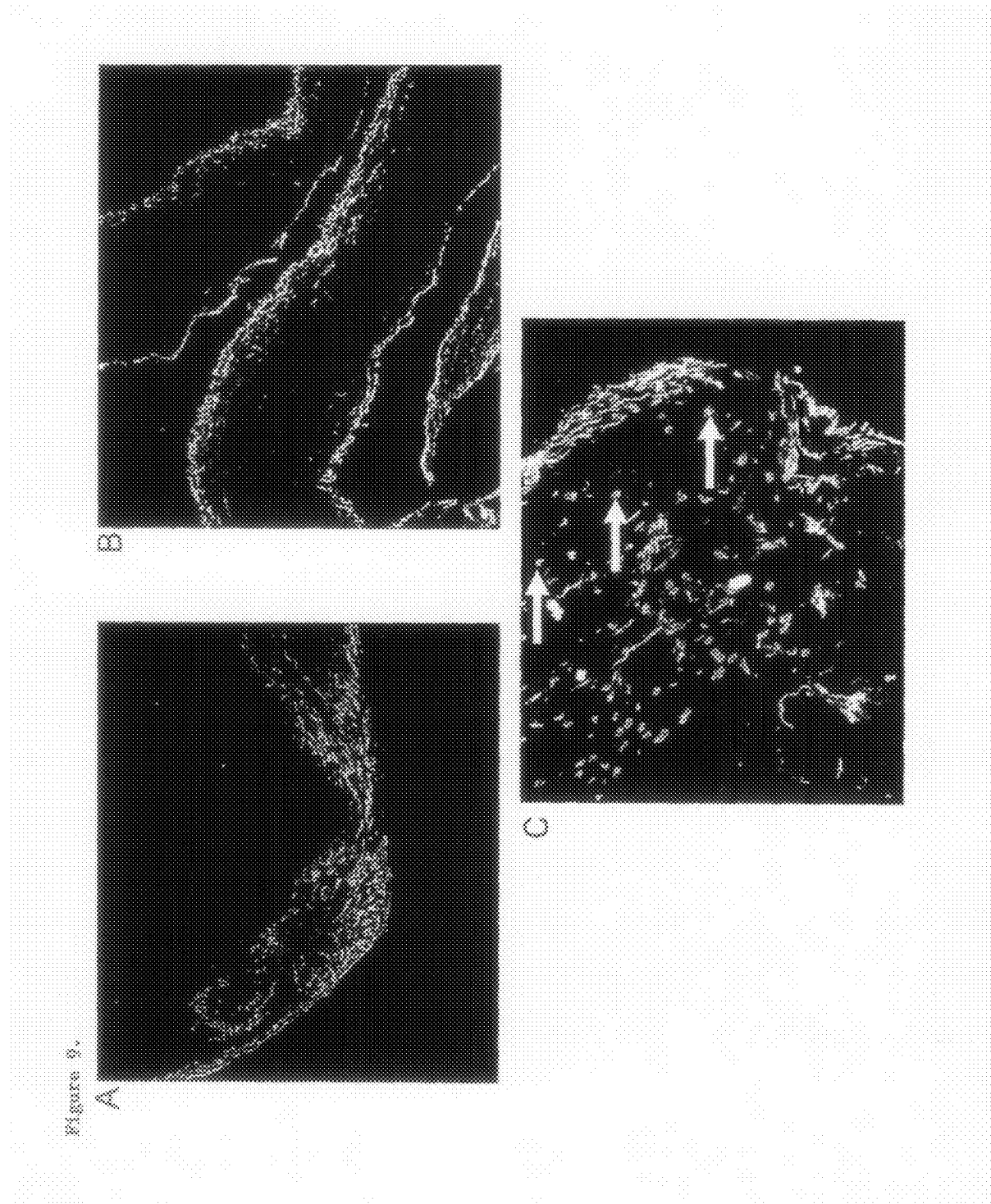

FIG. 7 shows the effect of phenytoin on collagen content and contraction. A) collagen content (μg/mL) of fibroblasts in monolayer treated with phenytoin for 21 days. B) effect of phenytoin on contraction of fibrin-based constructs;

FIG. 8 shows the effect of casting support on construct strength. This series of figures illustrates a construct subjected to mechanical testing to determine its ultimate tensile strength of a construct cast onto a glass slide (5 cm×2 cm); and FIG. 9 shows immunofluorescent staining for Collagen I in a construct.

Figure 10:
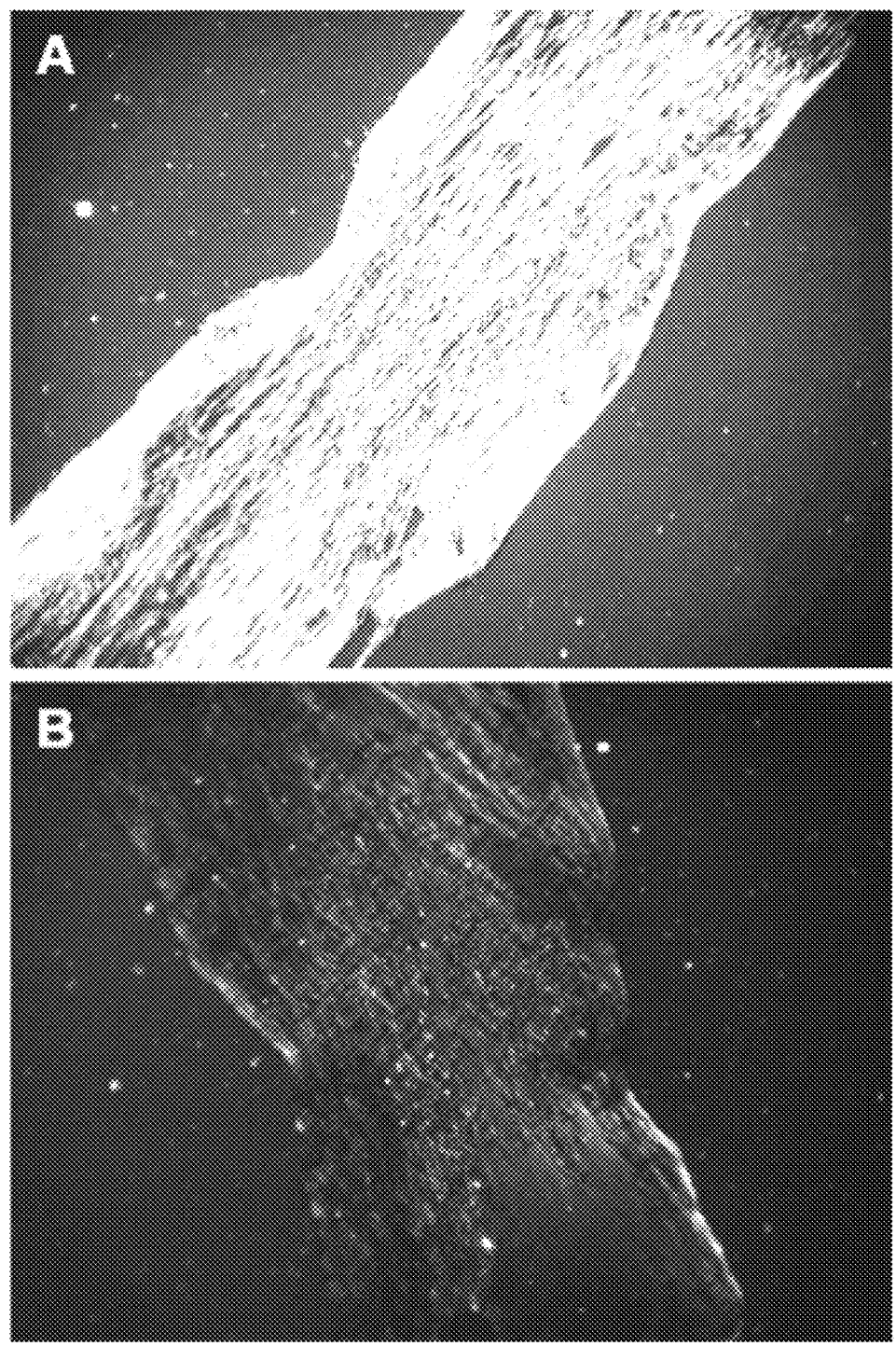

FIG. 10 shows that a construct (A) according to the invention has a high degree of fibrillar maturation of collagen compared to fibrin construct (B).

Figure 11:
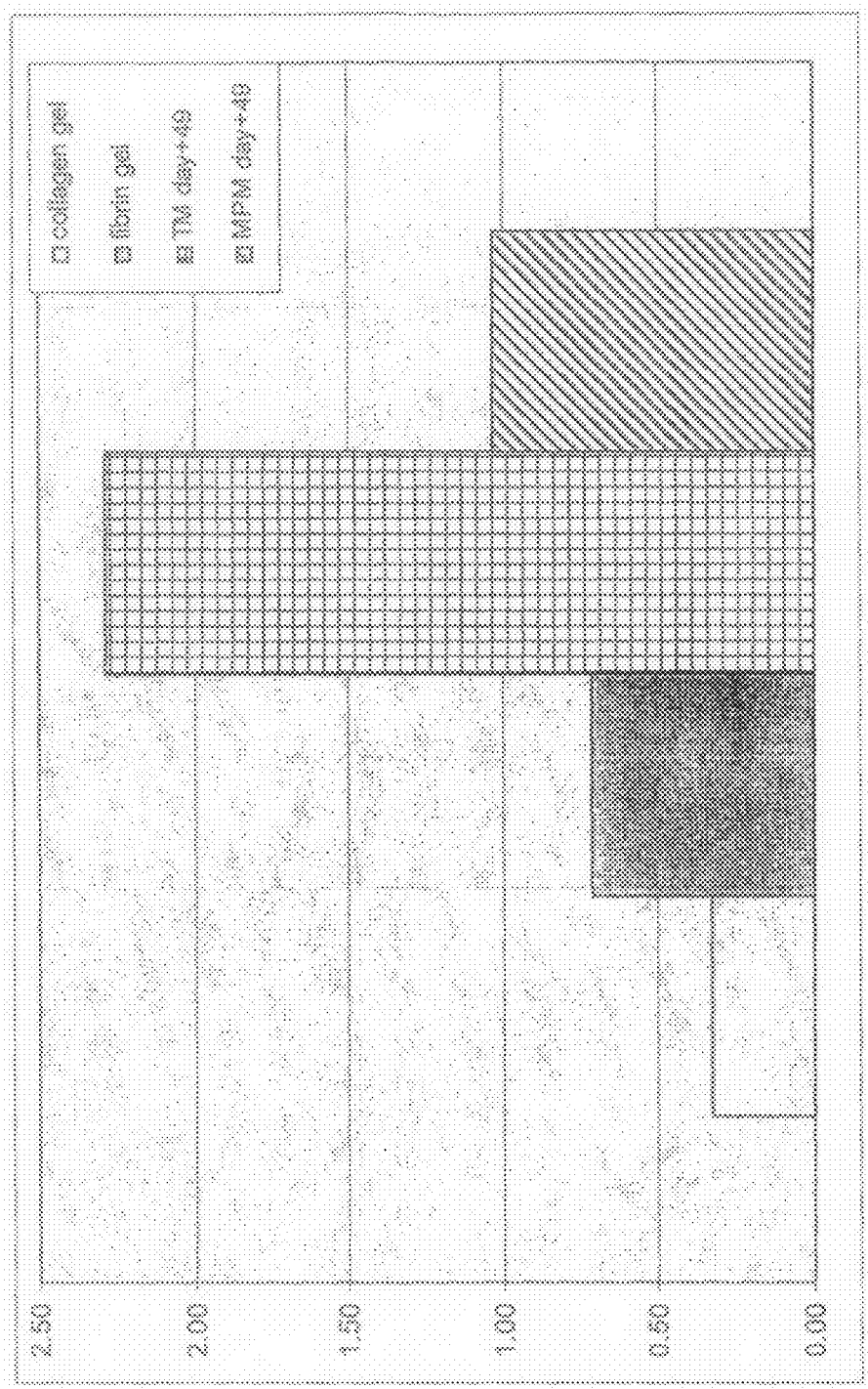

FIG. 11 shows that the collagen content increases with time.

Figure 12:
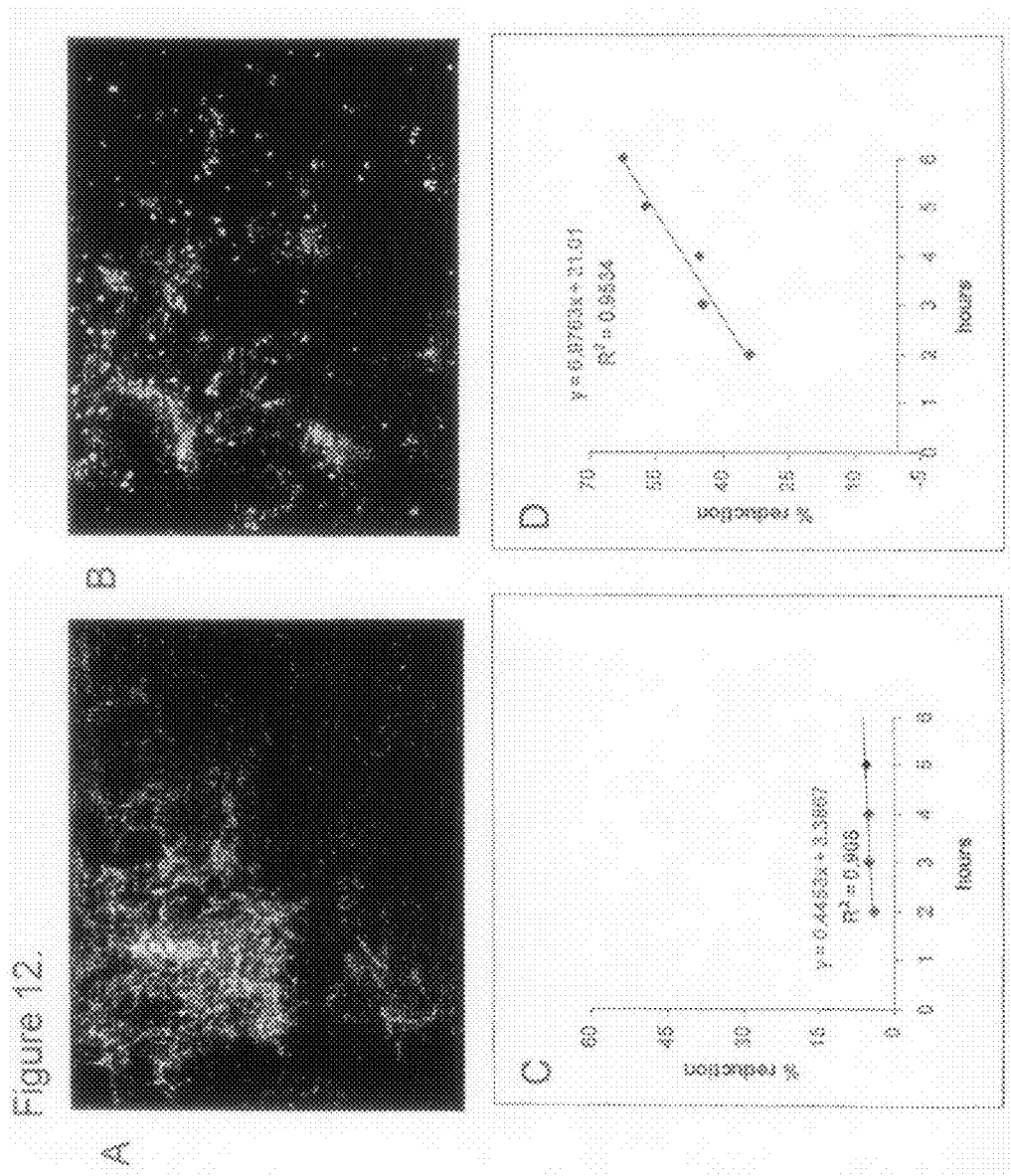

FIG. 12 shows freeze dried and re-hydrated constructs of the invention. (A) an example construct of the invention construct matrix viewed under UV illumination in which the fibrous nature of the structure is evident. (B) an example construct of the invention freeze dried, rehydrated and repopulated over 2 days with fluorescently labelled HDFs which have successfully attached to the construct. The cells are visible as bright spindle-shaped objects. (C) Metabolic activity of the freeze dried and re-hydrated construct as measured by Alamar Blue™ and presented as the percent of reduction of Alamar Blue over time (i.e. as the slope of the graph); (D) Metabolic activity of a freeze dried construct of the invention after rehydration and re-repopulation with HDFs over 2 days at 37° C., 5% $CO^2$ incubator presented as a function of the percentage of reduction of Alamar Blue™ over time (as before).

Figure 13:
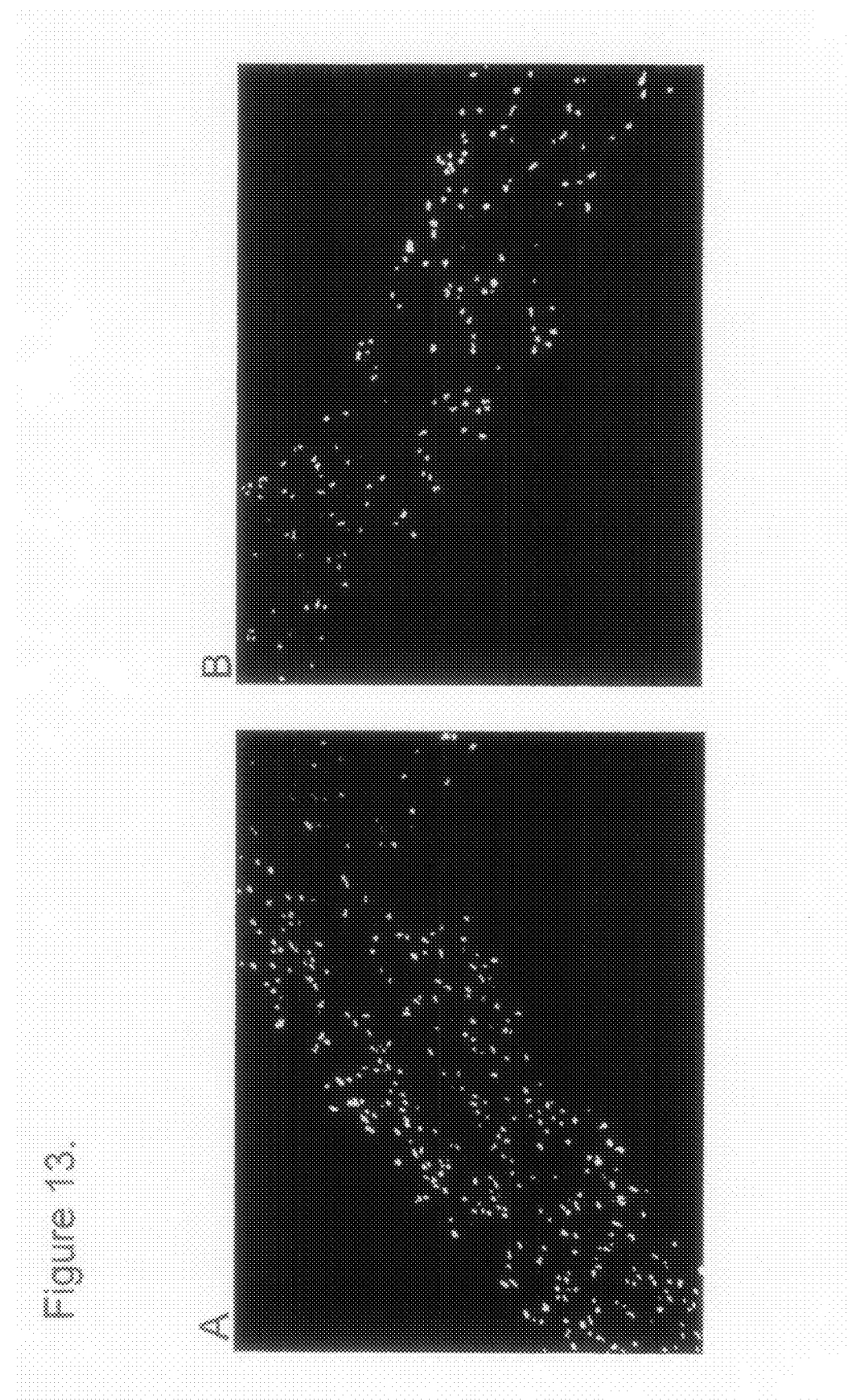

FIG. 13 shows cell remnants in freeze-dried constructs. Nuclear staining (DAPI) seen as bright points illustrate that nuclear debris are present in the air dried (A) and freeze dried (B) constructs of the invention. Although the debris remains, the constructs are dead of cellular activity as illustrated in FIG. 12 (B).

Figure 14:
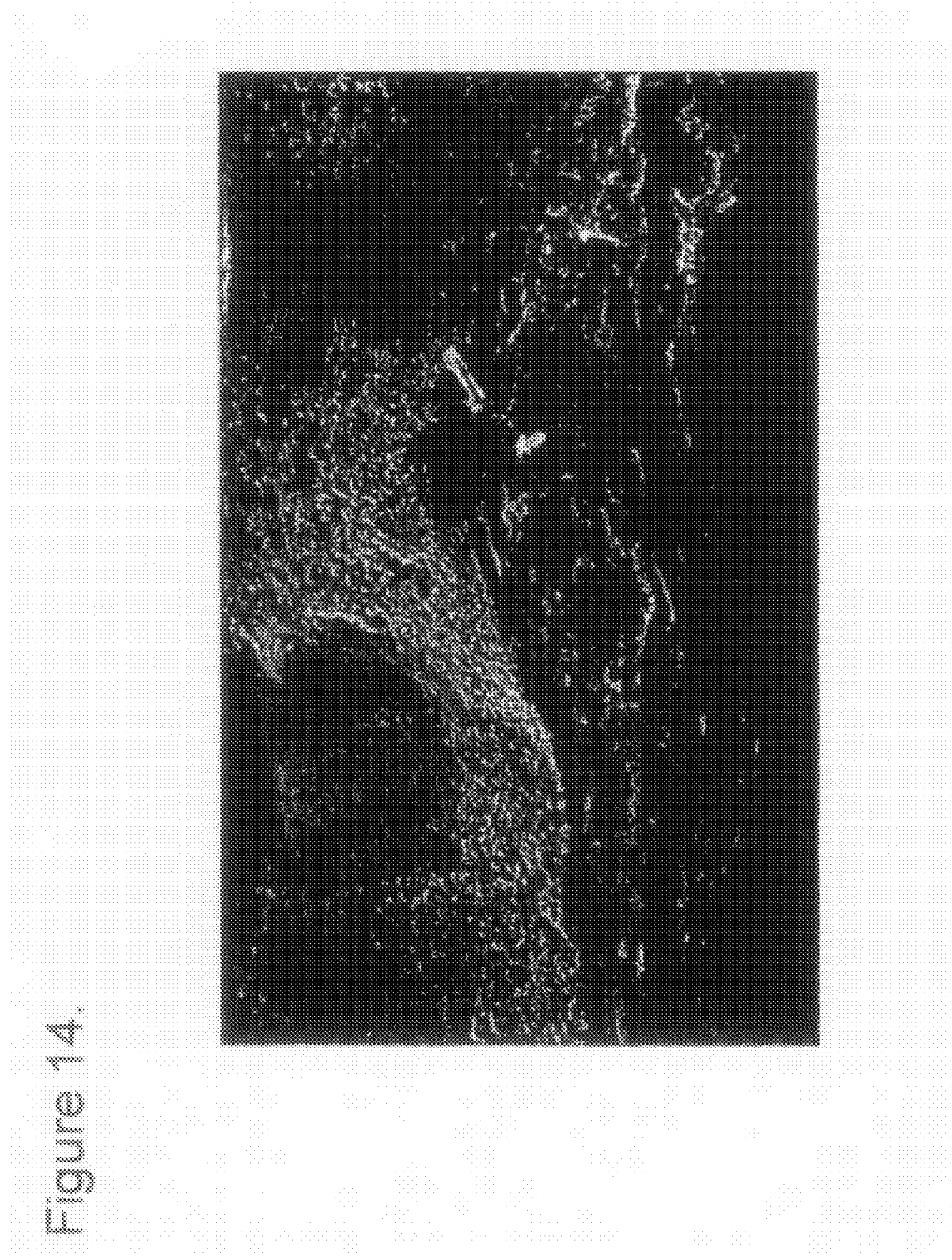

FIG. 14 shows a SEM image of a section through freeze dried non-repopulated construct of the invention. A cross-sectional scanning electron micrograph of a construct of the invention resemble showing the densely packed connective tissue fibres typical of the dermal layer of skin. By way of reference see, for example, Kessel and Kardon, [Tissues and organs: a text-atlas of scanning electron microscopy (1979). Publishers WH. Freeman and Co. p 149.]. Magnification 835×.

EXPERIMENTAL

A purpose of the present study was to investigate the basic requirements for and feasibility of producing a connective tissue equivalent or "construct", such as a wound-healing product that would closely resemble a skin graft or living skin equivalent for use in replacement of lost tissue. Unlike other applications currently available or anticipated in the advanced wound healing market (see for example Table 1 above), the present connective tissue construct ideally would be equivalent to a skin graft in wound healing capacity and would have similar permanence.

In general terms it may be understood that a skin replacement or skin equivalent of the present invention should preferably have one or two or more of the following broad specifications:
(1) Size range (4 $cm^2$-100 $cm^2$);
(2) Straight sides;
(3) Less than 2 mm thick;
(4) Must not fold on itself,
(5) Must conform to the wound site;
(6) Suturable, staplable, meshable; and
(7) Permanent replacement or permanent healing effect.

Skin has characteristic flexibility, tensile strength and elasticity. These features have not yet been achieved in vitro through tissue engineering to the same extent as it occurs naturally in skin. The connective tissue equivalent such as a living skin equivalent preferably has one or two or more of the following characteristics believed to be desirable, for example in the formulation of a tissue engineered skin replacement:
(1) Maximum strength, rigidity, elasticity, flexibility;
(2) Suturable, staplable, meshable;
(3) Minimum construct contraction;
(4) Maximum or optimal insoluble collagen (especially collagen I);
(5) Maximum or optimal ECM components (especially collagen III, elastin);
(6) Vascularisation potential;
(7) Potential to form a permanent skin replacement;
(8) Stable in storage; and
(9) Scalable.

Several ways of accomplishing these endpoints have been explored by the present inventors and they fall under one or more of the following broad categories:
(1) Media components (chemicals, growth factors, volume exclusion);
(2) Physical stimulation (electrical, tension, movement, ultrasound, infrared light);
(3) Bioreactor conditions (confluence, feeding regime, geometries); and
(4) Support systems (monolayer, fibrin, freeze-dried layer).

Preliminary experiments were conducted in which HDFs were seeded into or onto fibrin gels. Gels were cast into Petri dishes (approx. 8.3 cm diameter) or into TransWells (approx. 7.5 cm diameter) in which the gel/fibroblasts sit upon a polycarbonate filter. It was apparent from these preliminary experiments that, unless anchored in TransWells, gels contracted immediately upon gelation of the fibrin and continued to shrink maximally to 1 mm diameter sphere. That the fibroblasts in these gels remained viable was demonstrated by migration of the HDFs from the gels and proliferation during their time in culture to form a fibroblast sheet. Contraction of the fibroblast sheet itself was observed over the four-week culture period. In contrast, gels cast into TransWells did not contract during approximately 3 weeks in tissue culture until removed from the polycarbonate filter membrane at which point these contracted to the same extent as freshly made HDF/fibrin gels. However, contraction was prevented by fixing these constructs in formalin prior to removal from the TransWell membrane. Naturally, formalin-fixation also renders the cells non-viable.

Based on the preliminary experiments, further experiments as outlined below were designed.

Materials, Methods and Technical Aspects

Casting Parameters

Several prototypes for casting fibroblasts in fibrin have been and are being explored:
(1) 2.2 cm×2.2 cm (square) sterilised glass coverslips;
(2) 2 cm×2 cm (approximately), cast (freehand) directly onto the bottom surface of 6-well tissue culture dish; and
(3) 2.7 cm×3.3 cm (rectangular) cast directly onto the bottom surface of 8-well tissue culture dish.

Other Geometries/Variations Have Included:
(1) Fibroblasts/fibrin cast onto 2 cm×5 cm sterilised glass slides;
(2) Fibroblasts/fibrin cast within rectangle (2 cm×5 cm) inscribed onto polycarbonate membrane (0.4 µM pore size);
(3) Fibroblasts/fibrin or fibrin alone cast onto a base of previously cast fibroblast/fibrin constructs; and
(4) Fibroblasts/fibrin cast onto a base of freeze-dried (previously cast and matured) fibroblast/fibrin constructs.

In addition fibroblasts (without fibrin) have been cast directly onto:
24 mm diameter, 0.4 µM pore size, polycarbonate transwells.

The casting protocol of the present invention has been developed from Tuan et al. (1996) and Neidert et al. (2002), who describe inscribing a circle (8 mm diameter) onto the bottom of a plastic tissue culture dish to serve as a casting constraint for a mixture (in a 4:1:1 ratio) of fibrinogen, cells in tissue culture medium, and thrombin. Initially, casting the liquid mixture into the centre of the inscribed circle as described in the prior art resulted in the formation of a "dome" limited by the inscribed circle through surface tension at its boundary. However, thrombin cleaves fibrinogen and the resulting fibrin molecules assemble to cause gelation thus preserving the "domed" shape of the construct. This feature allows for "mechanically constrained compaction" required for fabrication of tissue engineered equivalents of sufficient "stiffness and strength" (Neidert et al., 2002). The fibrin matrix provided as the casting medium for these constructs provide a fibrillar network that can be aligned by the cells in the construct. Eventually the fibrin gel is remodelled and the fibrin is replaced by collagen I, the principal component of extracellular matrix (ECM) in skin, and other components of the ECM.

The constructs that we cast according to the novel prototype geometries described above, are scaled-up versions of the Tuan/Neidert constructs (see Table 2 below) where the height of the construct is estimated to be 1500 µM.

We have found that, in addition to circles, the constructs can be cast as squares or rectangles onto pre-made supports (e.g. coverslips, slides or membranes) or cast independently of support directly onto tissue culture plastic. However, it is important that during casting, the liquid mixture (fibrinogen, cells+medium, thrombin) does not contact the supporting walls of the vessel into which it is cast since this breaks surface tension and allows the liquid mixture to "creep" up the walls of the vessel. This results in a concave rather than the desired convex shape, and loss in height of the construct.

Prior to casting, the fibrinogen, thrombin, and cell mixture, are kept cold (on ice) in order to retard the process of gelation and to provide an adequate "window" to allow casting in the desired shape. Generally, casting is best performed by casting in the centre of the casting constraint and proceeding outwards so that sufficient "spread" of the mixture occurs before gelation. We anticipate that the casting dimensions described above will be scalable either by increasing the casting volume to make larger sheets or by using fibrin as glue to join several smaller constructs together (see below).

operator manipulation could be used to support the constructs and as a template or form for casting the construct into the desired shape, for example, plastic backing materials suitable for medical device applications, petrolated/paraffin gauze, or other membrane materials. The casting support should preferably be dry on the surface to which the fibrin mixture will be applied. The order of addition is: cells+medium, fibrinogen, thrombin. These two latter are kept cold on ice or a coolblock apparatus (2-10° C.) until addition to the cells. The correct number of cells for the size of construct (see Table 2) is resuspended in DMEM-10 medium of an appropriate volume. The fibrinogen is then added to the cells and gently mixed. The thrombin is added and the entire mixture is taken into a pipette of suitable volume and cast onto the support medium immediately. Once thrombin has been added, gelation should occur very rapidly. When using a preformed casting platform (e.g. glass coverslip), casting should preferably proceed from the centre of the platform and the liquid mixture should be allowed to fill the form through surface tension. Otherwise, if casting free-hand, an outline of the desired shape and size is cast onto the surface of the casting platform and the remainder is "filled in" by pipetting into the centre of the outline. Constructs are allowed to mature for 1 hour at 37° C. before addition of appropriate medium (DMEM-10 or Total) sufficient to cover the entire construct. Once cast, the constructs can be grown in media (as described below) for up to 9 weeks in one of the feeding regimes described below, in order to maximise collagen deposition, particularly collagen I, and other ECM components such as elastin.

Medium Components

The process by which constructs are influenced to deposit collagen and other ECM is called "maturation" and generally takes place over 3-9 weeks after casting. Many factors influence the deposition of collagen into tissue engineered skin equivalents. Among these are soluble growth factors and chemicals that can be added to the tissue culture medium in which the skin equivalents are grown. Fibrin induces the expression of collagen thus making an ideal base for constructing skin equivalents. In addition, fibrin entraps other

TABLE 2

Scale-up parameters for fibrin-based constructs.

| Dimension (mm) | volume (mm³) | Fold increase from 8 mm (volume) | Fibrinogen @ 5 mg/mL (µL) | Medium (µL) | Thrombin @ 25 units/mL (µL) | Cell Number | Final Volume (µL) |
|---|---|---|---|---|---|---|---|
| 8 mm diameter | 50 | 1 | 67.5 | 16.5 | 16.5 | $0.5 \times 10^5$ | 100 |
| 13 mm diameter | 199 | 3.9 | 263 | 64.5 | 64.5 | $2 \times 10^5$ | 392 |
| 22 × 22 square | 726 | 14.5 | 978 | 239 | 239 | $7.3 \times 10^5$ | 1,456 |
| 22 × 50 rectangle | 1,650 | 33 | 2,228 | 545 | 545 | $16.5 \times 10^5$ | 3,318 |
| 100 × 100 square | 15,000 | 300 | 20,250 | 4,950 | 4,950 | $150 \times 10^5$ | 30,150 |

Method of Casting

The constructs described in Tuan et al. (1996) and Neidert et al. (2002) used 100 µL of fibrinogen (5 mg/mL), cells in medium ($0.5 \times 10^6$/mL), and thrombin (25 units/mL) in a ratio of 4:1:1. Using the same formula, constructs according to one aspect of the present invention were cast onto (sterile) glass coverslips or polycarbonate membranes (0.4 µM pore size) or directly onto tissue culture plastic. Alternatively, other support materials lending a degree of rigidity convenient for soluble factors that can induce collagen deposition in the medium thereby enhancing and increasing local concentration of these within the construct itself.

A collagen-inducing medium for our constructs includes the following ingredients and was designated Total Medium (TM; supplier indicated in brackets):

3 parts Dulbecco's Modified Eagle's Medium (DMEM):1 part Hams F-12 medium (BioWhittaker or Cambrex))

2-10% NBCS or FCS (InVitrogen)

4 mM GlutaMAX 2 mM L-glutamine (InVitrogen)
5 ng/ml epidermal growth factor (Sigma Corp.)
0.4 µg/ml hydrocortisone (Sigma)
$1 \times 10^{-4}$ M ethanolamine (Fluka, #02400 ACS grade or Sigma)
  $+1 \times 10^4$ M o-phosphoryl-ethanolamine (Sigma)
5 µg/ml transferrin+20 pM triiodothyronine (Sigma)
6.78 ng/ml selenium (Sigma Aldrich Fine Chemicals)
0.2 µg/ml L-proline (Sigma)
0.1 µg/ml glycine (Sigma).

The following additional ingredients are known to induce further collagen synthesis and have been included in some experiments:
5 µg/ml insulin (Sigma); and/or
50 ng/ml L-ascorbic acid (Sigma); and/or
5 ng/ml epidermal growth factor (Sigma); and/or
5 µg/ml TGF-β (Sigma); and/or
0.05% PEG (Sigma); and/or
0.01 U/ml Plasmin (Calbiochem).

And, additionally or alternatively, in some experiments the collagen-inducing medium comprised:
10 µg/ml phenytoin (Sigma); and/or
25 µg/ml PDFG (Upstate Biotechnology).

Phenytoin is an agent known from other studies to induce collagen deposition, inhibit fibroblast contraction and positively influences vascularisation. However, phenytoin had not been tested in the production of a connective tissue construct and its possible effects there, particularly in combination with other factors, was uncertain.

PDGF is a fibroblast mitogen and induces collagen expression.

In some experiments a much simpler medium composition (DMEM medium), also known as proliferating medium, was used for reasons outlined below:
Dulbecco'sModified Eagle's Medium (DMEM) (Cambrex or BioWhittaker)
2-10% NBCS or FCS
4 mM GlutaMAX 2 mM L-glutamine.

During manufacture, raw materials may be required to conform to a higher standard than is generally required during the research and development phases of the invention. Table 3 lists the suppliers of clinical- or pharmacopoeia-grade raw materials used in the manufacture of the invention. For some materials no clinical- or pharmacopoeia-grade raw materials exist but the manufacturers may provide a certificate of analysis (including expiry date) for the material making it more suitable for use in the manufacture of clinical prototypes than materials used in research and development phases.

TABLE 3

Manufacturing grade supplier and grade of substance

| Substance | Supplier | Grade |
| --- | --- | --- |
| Dulbecco'sModified Eagle's Medium (DMEM) | Cambrex | cGMP |
| Hams F-12 medium | Cambrex | cGMP |
| NBCS or FCS | JRH | EDQM |
| 0.4 µg/ml hydrocortisone | Spectrum | USP |
| 5 µg/ml transferring | Serologicals | CEPS |
| 0.2 µg/ml L-proline | Molekula | Ph Eur |
| 0.1 µg/ml glycine | Molekula | Ph Eur |
| 5 µg/ml insulin | Serologicals | Ph Eur |
| 50 ng/ml L-ascorbic acid | Molekula | Ph Eur |

Feeding Regimes, Confluence of Cells, Passage Number, Type of Cells

Neidert et al (2002) noted an increase in collagen content, elastic and ultimate tensile strength of their fibrin-based constructs when their growth medium was replaced three times per week relative to when it was replaced once per week. However, in addition to replacing spent ingredients and removing potentially harmful metabolites and catabolites, we considered that medium changes might also remove the "building blocks" for complex molecules such as those found in the ECM. In addition, we considered that any activity that perturbs the "status quo" in medium conditions is a potential stressor on cells and this may have both positive and/or negative influence on cell behaviour. Changes to the frequency and components used at each medium replacement might thus have an effect on collagen, and other ECM, deposition.

Constructs were grown for 3-9 weeks in various culture conditions including:
(1) Repeated cycles of serum starvation (DMEM medium+ 0.1% NBCS or FBS) 3 days, TM 3 days;
(2) DMEM medium (0-4 weeks) followed by TM for (5-9 weeks);
(3) DMEM medium (0-4 weeks) followed by TM, ±phenytoin, ±PDGF, for (5-9 weeks).

Furthermore, using these various medium compositions, constructs were fed once, twice, or three times weekly. In addition, not all ingredients were included in all medium changes. For example, labile ingredients such as PDGF, TGF-β, and EGF, might be added at every medium change, once per week, once every three weeks, once at three weeks and again at seven weeks. Alternatively, rather than removing the entire spent medium at each medium change, the spent medium might be supplemented with fresh medium or fresh factors, in order that accumulating beneficial factors might remain in the medium. Alternatively, spent medium could be removed and replenished through a continual flow system operating over the constructs such that medium is replaced daily, half-daily, or hourly or as demanded by a biofeedback system monitoring the medium components.

In addition to the components of the medium, the cell number was influenced by the feeding regime undertaken in these experiments. For example, cells subjected to TM would be more likely to synthesise and deposit collagen whereas cells subjected to DMEM medium would be less likely to synthesise collagen but more likely to proliferate in the constructs. Thus, the longer cells were held in DMEM medium before switching to TM, the more cells would accumulate in the construct. In addition, in certain construct geometries, contraction was minimised by initial incubation in DMEM prior to switching to TM.

Finally, the age (or passage number) of cells may influence their ability to proliferate, express and deposit collagen and other ECM, and to contract the skin equivalent, therefore passage ("p") number (p6-p15) was another parameter tested in our constructs. Similarly, although the constructs were usually composed with HDFs and culture conditions used in the experiments favoured the growth and survival of these cells, it is possible that a component of other cell types might influence the ability of HDFs to make and deposit collagen and other ECM. Normally, the HDFs used in the constructs are derived from human neonatal foreskin. A mixture of cells exist in the intact tissue and in order to isolate the HDFs from the other cell types a combination of enzymatic digestion and growth medium is used to favour outgrowth of HDFs. After six passages, the majority of cells (>90%) thus treated are HDFs. In order to include other potentially beneficial cell types in the constructs, human neonatal foreskins were enzymatically digested to yield a suspension of cells and, rather than putting these into tissue culture, they were cast immediately into fibrin based constructs.

End Products

Once constructs of the invention have been maximally matured they are removed from tissue culture and may be treated in one or more of several ways:

(1) Packaged for shipment in product transport medium;
(2) Keratinocytes added to the surface and further maturation prior to packaging in product transport medium for shipment;
(3) Freeze-dried and packaged dry for shipment;
(4) Freeze-dried and packaged for storage up to 18 months;
(5) Freeze-dried and repopulated with cells (fibroblasts and/or keratinocytes) and fibrin, packaged for shipment in product transport medium; and/or
(6) Freeze-dried and repopulated with cells (fibroblasts and/or keratinocytes) and fibrin, matured further, then packaged for shipment in product transport medium.

Any of these products may be cut to a desired shape and size.

Each of these endpoints may have a particular clinical application(s). In addition, various growth factors (for example, VEGF) or chemical substances may be added to the final (shipped) product so that when placed in situ, vascularisation is induced.

At the end of the maturation period, constructs may be made more robust and resistant to degradation in the wound by cross-linking using chemical means or by exposure to ultraviolet light.

In addition, a sample of the final products (after maturation) is assessed for physical and biochemical characteristics such as content or presence of collagen I, collagen III, and elastin, and for tensile and elastic strength, gene expression profile (especially genes generally believed to be involved in wound-healing). In addition, parameters such as the potential of the construct to induce vascularisation or to persist in the wound environment may be tested using surrogate modelling systems.

Method of Measuring Collagen Content of Constructs
Sircol Assay

Appropriate standards (0-500 μg/ml of collagen) should be prepared. Samples must be in medium that contains less than 5% serum. This is particularly important if assaying media, as soluble collagen will be produced in it. In order to solubilise collagen, samples should be digested in 1 ml 5 mg/ml pepsin (in 0.5 M acetic acid) overnight at room temperature. If solutions are clear with no visible particulate matter, proceed with the Sircol assay. If cloudy or containing particulate matter, proceed as follows:

Samples should be passed through a 1 ml syringe and a series of needles, from around 19 gauge to finally a 26 gauge. If sampling monolayer cultures, this procedure should be done in the pepsin solution, but prior to overnight digestion.

Samples should then be incubated for >1 hour at 37° C.

Briefly spin samples in a microfuge at 14,000 g to pellet cell debris.

Samples of supernatant may then be taken for the assay.

Remaining insoluble collagen requires heat denaturation to yield gelatine in which case samples should be placed at 80° C. on a heat block for around 20 mins.

Samples should be assayed immediately using the Sircol Soluble Collagen Assay (Biocolor UK). Otherwise, samples can be snap-frozen in liquid nitrogen for later analysis of collagen content.

Method of Measuring Ultimate Tensile Strength and Elastic Strength

Connective tissue constructs such as skin equivalents can be examined to assess their suitability to act in the target area, for example as a skin replacement. Skin equivalent constructs should possess characteristics and dynamics appropriate for the role of skin replacement in strength, elasticity and durability.

Stretching and stretch cycling of constructs are used to determine elasticity modulus, yield point, elastic limit, proportional limit and breaking point. These would be calculated using appropriate instrumentation and computer software (Mecmesin). 'Boring' or 'inflation' analysis (Stable Microsystems Ltd.) can be used to determine lateral stretch and lateral deformation values of constructs. This is carried out by either inserting a probe laterally through the constructs (boring) or by weighing down the edges and applying air pressure through the middle of the construct (inflation). Permeability may also be assessed in a test similar to inflation assay. Compression and hardness may be assessed using probing techniques.

Constructs are placed on a strength-testing device, either alone or on a supportive backing material, such as glass slides. Alternatively, constructs may also be sutured at the corners so that they can be manoeuvred into place between clamps positioned at the stretch points. The constructs are grasped between the two clamps, oriented horizontally or vertically, on the machine. Software supplied with the machine allows for a range of variables to be tested, such as rate of movement (2-10 mm/minute), applied force ($5 \times 10^5$-$5 \times 10^7$ dynes/$cm^2$ cross-sectional area), Young's modulus.

Method of Assessing Gene Expression
Isolation of Total RNA

Wash constructs in 10 ml cold PBS and transfer to a centrifuge tube. Remove PBS and 1-2 ml of Tri-reagent (Sigma T-9424). Vortex briefly and leave at room temperature (or 37° C.) for 5-15 min. Transfer the liquid to a 1.8 ml eppendorf tube. Add 200 μl chloroform for each 1 ml Tri-reagent.

Shake well (do not vortex) and leave at room temperature for 15 min. Centrifuge at 13,000 rpm (Beckman Allegra 21R centrifuge) at 4° C. for 15 min. Transfer upper phase to a new tube. Avoid taking any of the white lower layer. Add 500 μl isopropanol for each 1 ml of Tri-reagent.Mix by inversion and leave to stand for 10 min at room temp. Centrifuge at 13,000 rpm at 4° C. for 15 min. Pour off supernatant and resuspend pellet in 75% ethanol. Centrifuge at 13,000 rpm at 4° C. for 15 min. Repeat the washing step. Remove 75% ethanol and allow to air dry for 10 min (do not over-dry). Dissolve pellet in 50 μl of RNAse free water (DEPC-treated or Sigma W-4502). Determine the yield and concentration of RNA.

Conversion of RNA to cDNA

In a 1.8 ml eppendorf tube mix, 1 μg RNA, 1 μl Oligo dT (20 pmol/ml; Roche), RNase treated water (DEPC-treated or Sigma W-4502), to give a final volume of 29 μl. Incubate at 70° C. for 8 min. Centrifuge briefly and place on ice for 10 min. To each tube add:

8 μl MMLV-RT buffer (5× Promega)
1 μl MMLV-RT H (200 U/μl, Promega M3681)
2 μl dNTP (stock 25 mM made from set of dNTP 40 μmol Promega U1240).

The reaction proceeds for 2-3 hours at 37° C. followed by 2 min at 95° C. The products can be stored at −20° C.

Alternatively, if the cell number or RNA retrieved is expected to be low, RNA can be subjected to a polyA PCR reaction in order to globally amplify all polyadenylated mRNA in the sample (Brady & Iscove, 1993, Methods Enzymol. 225: 611-623). Cells (up to $10^5$ cells) are lysed or RNA (0.1-100 ng) resuspended in 10 μl DL buffer [1 ml 5× RT buffer (InVitrogen), 10 μl 20 mg/ml BSA (Roche, molecular biology grade), 250 μl nonidet P-40 (10%, NP-40, Roche), 3.55 ml RNAse-free water (Sigma)], 4 μl Rnase inhibitor (Ambion), 4 μl Prim mix [5 μl PM (800 μl 2.5 mM dNTP's (Roche), 24 µl dT24 (200 µM or 40 OD units/ml) Not1-OligodT), 20 µl water]. Samples are then denatured at 65° C. for 1 minute, allowed to cool for 3 minutes at ambient temperature, then placed on ice. Add 0.5 µl M-MLV Reverse Transcriptase (RNase H⁻) to each sample and incubate as follows: 15 min at 37° C., 10 min 65° C., then place on ice. The first strand cDNA is then treated with Terminal Deoxynucleotidyl Transferase in order to polyadenylate the 3' end of the first strand product by adding an equal volume of 2× Tailing Buffer [1 ml Tailing buffer 5× (InVitrogen), 25 µl dATP (100 mM; Promega), 1.475 ml water (Sigma)] and 0.5 µl TdT (InVitrogen). The tailing reaction proceeds by incubation for 15 min at 37° C. followed by 10 min at 65° C. and is then placed on ice. Finally the tailed first strand cDNA product (5 µl) is amplified by addition of 10 µl of PCR mix consisting of 100 µl 3M buffer [1 ml 10× Taq Buffer (Roche), 375 µl dNTP's (25 mM, Roche), 10 µl BSA (Roche, molecular biology grade), 100 µl 10% Triton X-100 (Roche), 20 µl $MgCl_2$ (1M), 2.35 ml molecular biology grade water], 5 µl Not1-Oligo dT (200 µM) primer, and 3.75 µl Taq Polymerase (Roche or Promega). The reaction proceeds through cycles (25) of incubation 1 min at 94° C., 2 min at 42° C., 6 min at 72° C., followed by further cycles (25) of incubation 1 min at 94° C., 1 min at 42° C., 2 min at 72° C.

Gene-Specific PCR

In order to assess expression of specific genes, PCR is performed using specific primers designed to amplify the gene of interest. Genes of interest include human, for example, plasminogen activator inhibitor I, platelet derived growth factor, collagen IA1, collagen 3A, collagen 4A2, collagen 6A1, elastin, Ki67, and CDC6 and comprise genes whose expression is involved or influenced in wound healing, gene expression, proliferation, collagen expression, metabolism and biochemistry, or indicative of these processes.

Using appropriate primers (MWG), conventional (non-quantitative) PCR amplification is carried out in the following reaction conditions for each 2 µl cDNA sample:

| | |
|---|---|
| 10× PCR buffer with $MgCl_2$ (Roche) | 2 µl |
| 2 mM dNTPs (Promega) | 2 µl |
| Forward primer (100 µM) | 0.4 µl |
| Reverse primer (100 µM) | 0.4 µl |
| Taq polymerase | 0.4 µl |
| Water (Sigma W-4502) | 12.8 µl |

The mixture is heated to 95° C. for 5 minutes then subjected to incubation cycles (20-35) of 50 seconds at 94° C., 1 min at 60° C., 2 min at 72° C., followed by incubation at 72° C. for 10 minutes.

Alternatively, the each cDNA sample (diluted 1:1000 in molecular biology grade water) can be subjected to semi-quantitative Realtime PCR amplification (ABI 7700 Taq-Man) in a total reaction volume of 15 µL consisting of:

| | |
|---|---|
| cDNA (diluted 1:1000) | 10 µL |
| H2O | 5.925 µL |
| 10× buffer (Oswel qPCR core kit, RT-QP73-05WR) | 2.5 µL |
| 25 mM MgCl2 | 3.5 µL |
| 2.5 mM dNTPs | 2.0 µL |
| 100 µM Forward Primer | 0.225 µL |
| 100 µM Reverse Primer | 0.225 µL |
| 100 µM Probe | 0.05 µL |
| Taq polymerase | 0.125 µL. |

Method of Immunohistochemical and Histochemical Staining for Collagen and other ECM Components Samples for immunohistochemistry were snap-frozen in an isopentane bath held over liquid nitrogen, in OCT compound (R. A. Lamb) and stored at −80. Sections (8 µm) were cut and air dried onto glass slides. Sections were overlaid with control or test antibody (e.g. AbCam Laboratories; anti-collagen I antibody ab6308, anti-elastin antibody ab9519, anti collagen III antibody ab 6310) diluted in PBS (containing 10% BSA) at predetermined concentrations and incubated for 30 minutes at RT. Sections were washed before being incubated with Anti-mouse Ig-FITC or Anti-mouse Ig-FITC-streptavidin (at pre-determined dilution in PBS containing 10% BSA; Jackson Immunoresearch) for 30 minutes at RT. Following a final wash slides were mounted in UV free aqueous mountant.

Samples for histochemistry were prepared by embedding in paraffin following standard protocols and sectioned using a microtome (5 µm). Remove wax from sections by transferring sections through four changes of xylene in fume hood (5 minutes in each for soft tissue). Sections were rehydrated in three changes of 100% I.M.S and one change of 95% I.M.S, followed by rinsing in running tap water.

To visualise collagen (blue) and fibrin (pink) in the constructs, Masson's Trichrome stain was used. Sections were stained in celestine blue solution for 5 minutes and rinsed in distilled water, then stained in an alum haematoxylin (e.g. Mayer's or Cole's) for 5 minutes. Samples were then washed in running tap water until blue. Sections were differentiated by dipping in 1% acid alcohol for 4 seconds then returned to running tap water. Next sections were stained in acid fuchsin solution for 5 minutes and rinse in distilled water, then treated with phosphomolybdic acid solution for 5 minutes, drained, and stained with methyl blue solution for 2-5 minutes and rinsed in distilled water. Sections were treated with 1% acetic acid for 2 minutes, dehydrated through one change of 95% I.M.S and three changes of 100% I.M.S for approximately 2 minutes in each. Finally, samples were cleared in four changes of xylene for 1-2 minutes each and mounted in DPX and coverslip.

Results

The results are shown in accompanying FIGS. 1 to 9.

Figure 1:
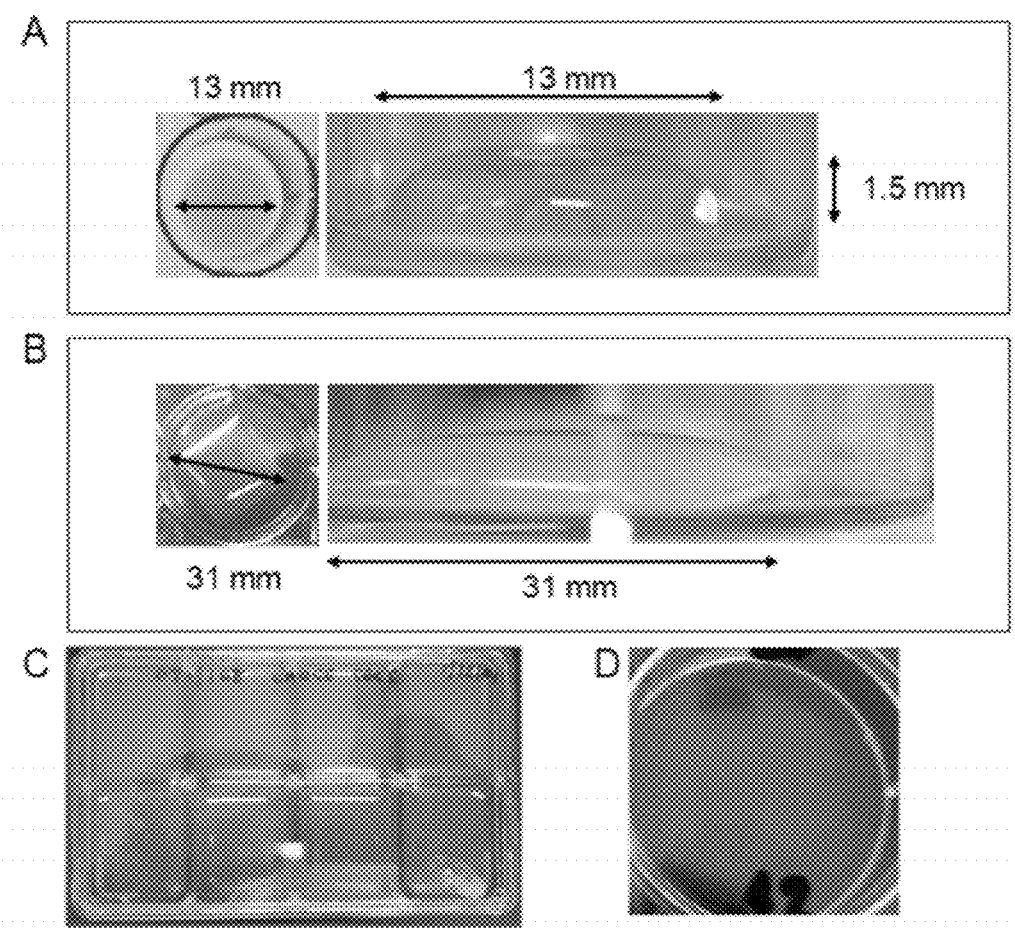

In FIG. 1 all of the illustrated constructs are constrained in the horizontal direction and are approximately 1.5 mm in height. Note that constructs illustrated in FIGS. 1C and D, are 42 and 50 days post-casting, respectively, and have not contracted appreciably.

Figure 2:
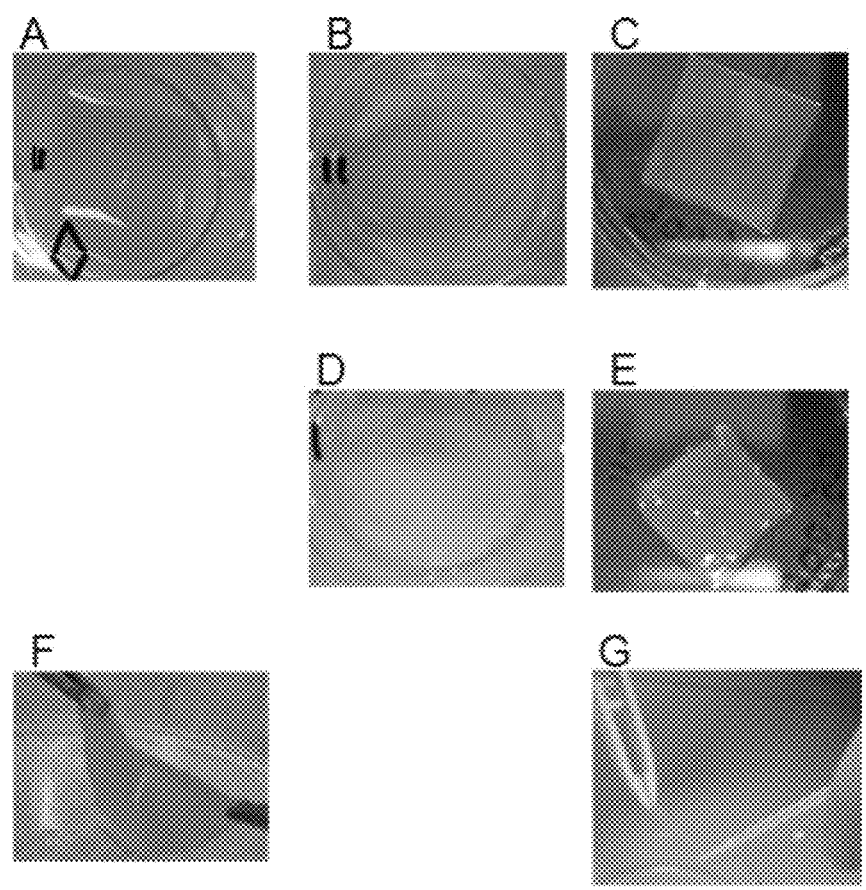

It is clear from the illustrations in FIG. 2 that over time and under medium conditions intended to boost collagen, that the constructs lose translucency and become considerably more opaque indicating that collagen has accumulated in the constructs (compare A, B, C). In addition, the construct at 43 days post-casting (E) maintains its shape when released from its constraint (in this case the glass coverslip) whereas a similar construct (D) contracts dramatically when released from constraint on day 17 post-casting, illustrating that by day 43 the construct has gained internal structure and rigidity. Finally, manipulation of constructs on day 0 (F) and day 43 (G) post-casting demonstrates that strength and elasticity have been gained in the matured constructs.

Figure 3:
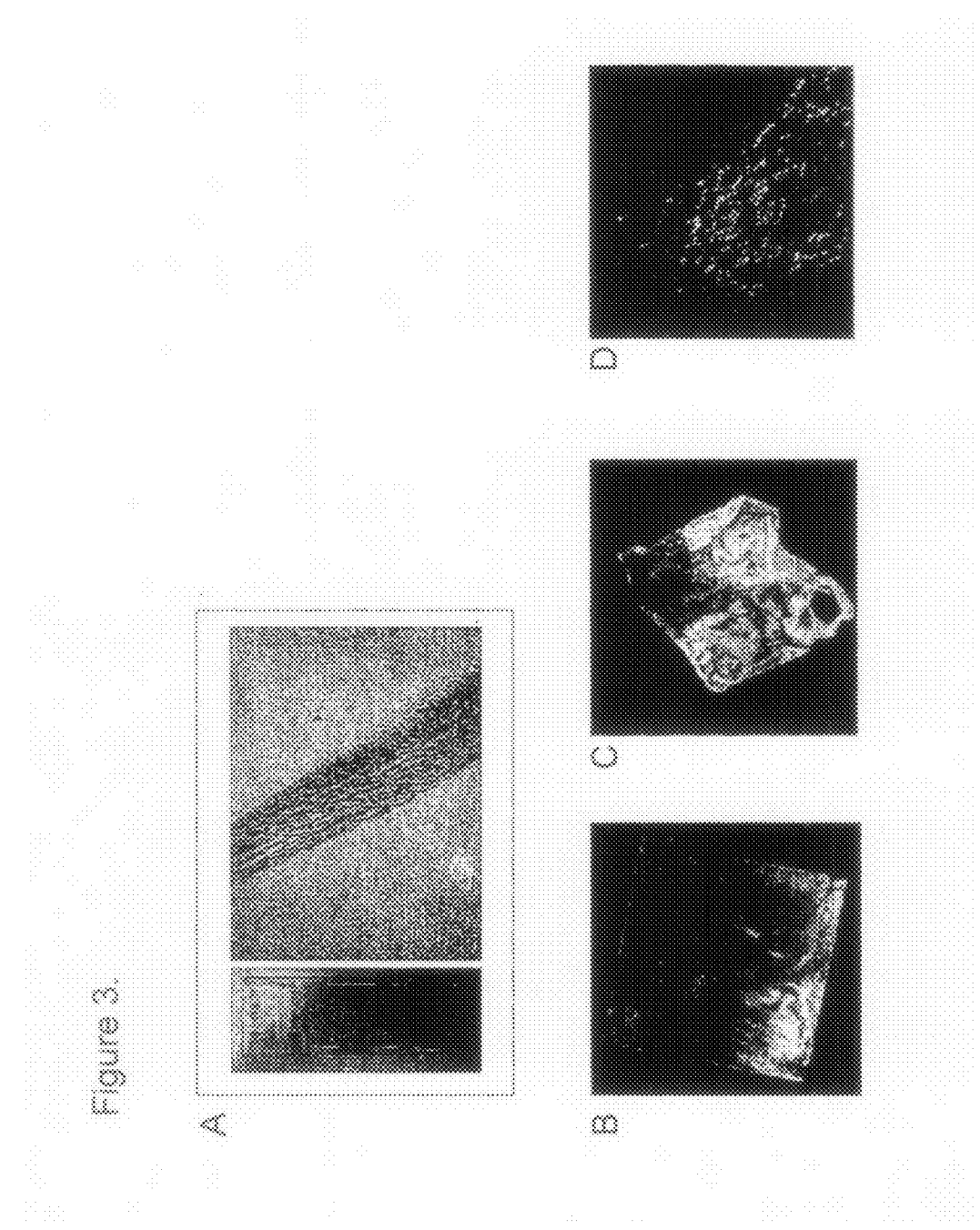

During the process of maturation, the collagen content of constructs increased and this is evident in FIG. 3 (A) in which Trichrome stain has been used to visualise collagen (blue) in the constructs, and FIG. 3 (D) in which a matured construct can be seen exhibiting birefringence, a property of matured collagen fibrils. Although rigidity can be provided by underlying supports such as coverslips, as in FIG. 3 (B), as seen in FIG. 3 (C), constructs freeze-dried in the absence of underlying supports also retain some rigidity.

Figure 4:
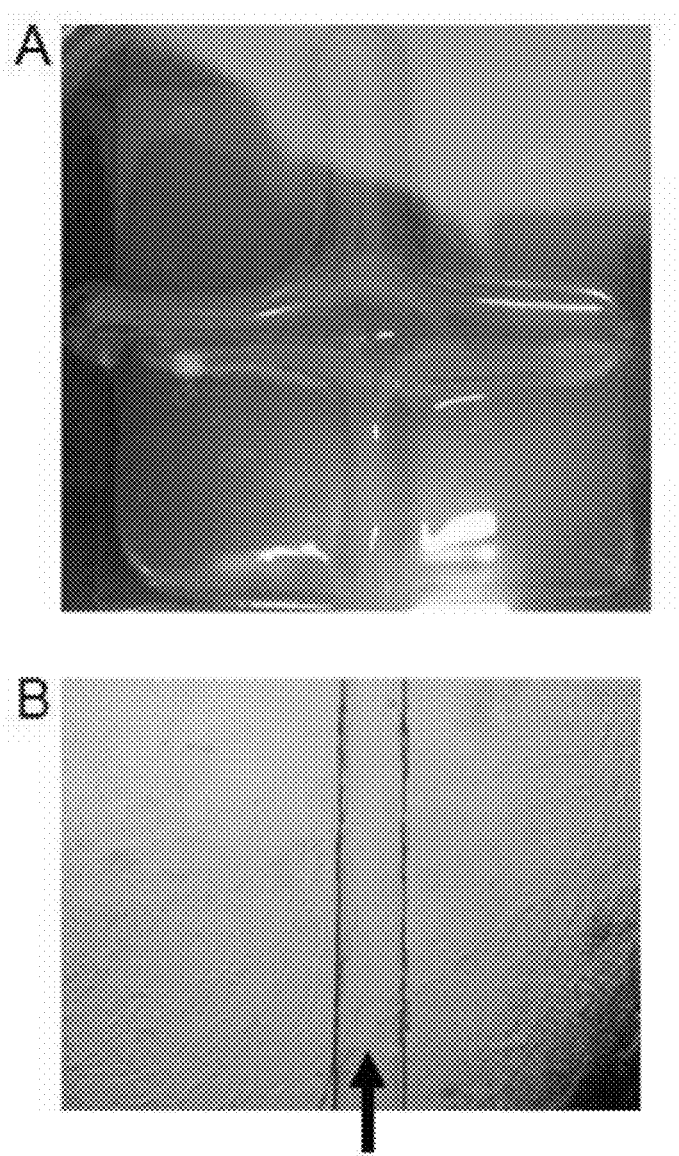
FIG. 4 shows scale-out of constructs. A) four individual constructs cast onto 2 cm×2 cm coverslips, with cell-free fibrin cast between each construct and B) magnification of the junction between two such coverslips approximately 14 days post-casting.

A scale-out of constructs is shown in FIG. 4. One approach to making larger constructs would be to "stitch" several smaller constructs together to make a sheet of constructs resembling a sheet of postage stamps. In order to secure the constructs together the bridges between each construct were constructed of cell-free fibrin so that fibroblasts would be induced to migrate into the bridge and "stitch" one construct to its immediate neighbours as shown in FIG. 4(B). The arrow in FIG. 4(B) indicates that fibroblasts have colonised the inter-construct fibrin bridge. The lines to the right and left of the arrow are the edges of the coverslips of two neighbouring constructs.

It is important for constructs be constrained in order for cells to align the collagen as it accumulates in the constructs. However, as illustrated in FIG. 2(D), if the constraint was released before it was fully matured, release of the tension that constrains the constructs caused the fibroblasts to contract the construct irreversibly. We tested various media formulations and feeding regimes on constructs cast onto 2 cm×2 cm glass coverslips and a summary of these experiments is illustrated in FIG. 5.

Figure 6:
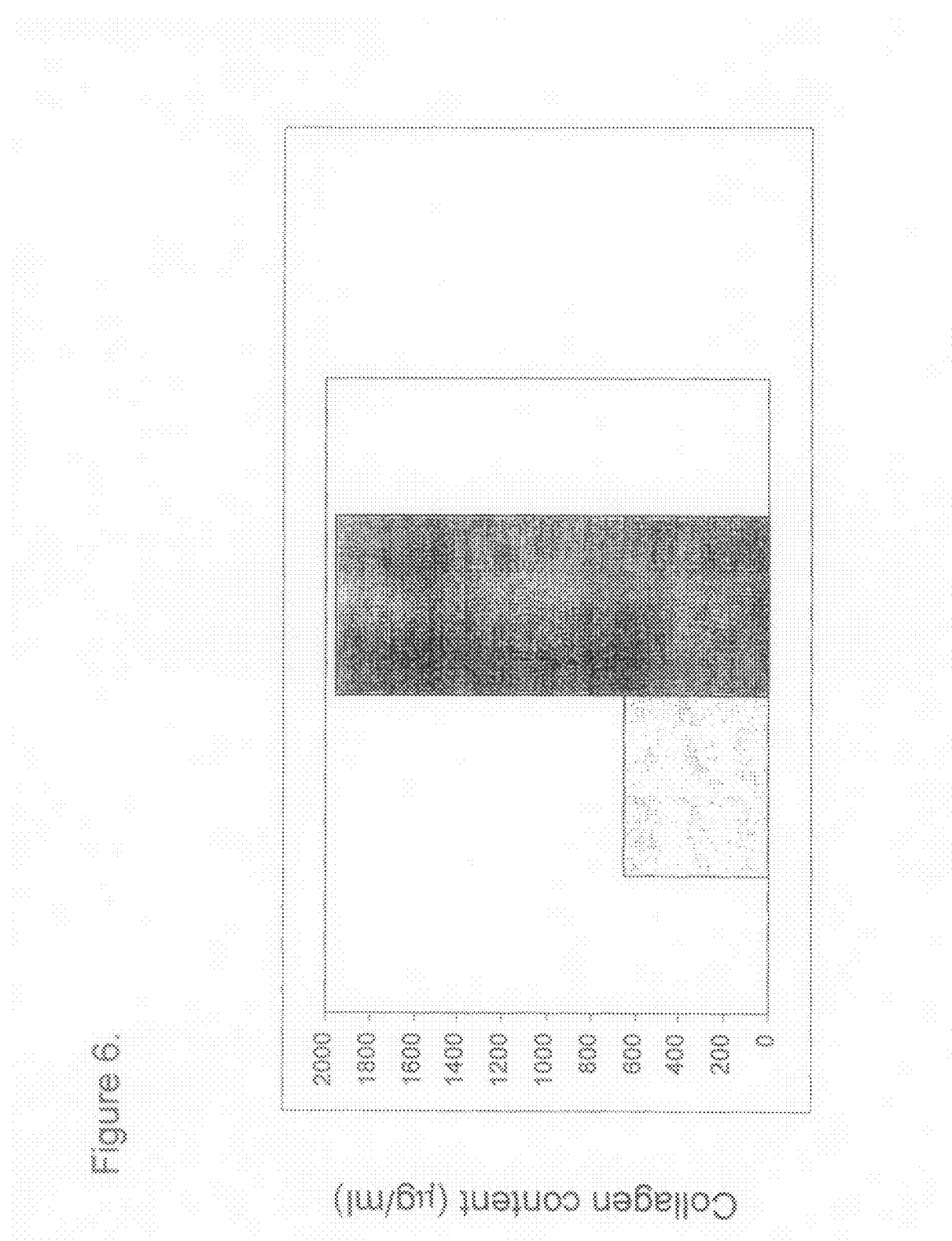
FIG. 6 shows an estimate of collagen content in matured constructs. The figure illustrates that fibrin-based constructs (right hand bar) accumulate considerably more collagen than fibrin-free constructs cast directly into transwells (left hand bar)

In FIG. 6, an estimate of collagen content in matured constructs is shown. The constructs were cast directly into transwells. In addition, the fibrin-based constructs were matured in medium that was supplemented with TGF-β1 and plasmin. All other medium components and feeding regimes were identical.

Phenytoin is one of many factors that affect collagen expression or deposition. In some experiments, we included 10 μg/ml phenytoin to the medium since we had demonstrated previously (se FIG. 7(A)) that this was the optimal dose to increase collagen deposition by cells. A second effect of phenytoin is illustrated in FIG. 7(B), namely that phenytoin reduces contraction of constructs released from constraint (in this example, a 2 cm×2 cm glass coverslip. The construct on the left was incubated in growth medium without phenytoin while the construct on the right received 10 μg/ml phenytoin in the growth medium.

The series of photographs in FIG. 8 shows a construct subjected to mechanical testing to determine its ultimate tensile strength of a construct cast onto a glass slide (5 cm×2 cm). A) The glass slide supporting the construct breaks under tension (small arrows), the construct begins to stretch (large arrow), B) the construct continues to stretch, C) the construct loses structural integrity and ultimately it breaks.

FIG. 9 illustrates the construct fixed and processed as described above in order to visualise the presence and architecture of collagen I deposited by HDFs in the matured construct.

This data clearly confirms that, under the conditions used in these experiments, HDFs deposit collagen I into the constructs and that this lends structure to the constructs.

EXPERIMENTAL EXAMPLES

Structural complexity of SKN constructs increases with time and maturation. Constructs were cast by embedding human dermal fibroblasts within a fibrin matrix and incubated in Total Medium for up to 49 days (as described previously). The medium was changed every 2-3 days and the constructs were analysed using histological techniques. Results showed that ultrastructural changes occurred during this 49 day maturation period. After 11 days, histological staining with the combined MSB stain demonstrated that the original fibrin had been largely replaced by collagen. However, at this early stage in the maturation process, there was little evidence of structural integrity as no ultrastructural features were noted on microscopic examination. At 21 days post-casting, histological examination revealed that the fibrillar structure of collagen was developing in the constructs. However, some areas remained devoid of fibrillar content indicating that these had yet to completely mature. Histological staining of sections from constructs after 49 days of maturation revealed significant fibrillar content throughout the constructs. Further changes in medium beyond 49 days did not appreciably enhance the ultrastructural content of the constructs but could serve instead to maintain the structure that had already developed.

The preferred incubation/maturation times are therefore a minimum of 21 days and a maximum of 63 days. Most preferable would be 21-49 days, 21-35 days, 21-29 days.

Resistance of Constructs to Digestion in Wound Emulation Environment (Evidence to Support Healing by Primary Intent).

Fluid found in acute wounds is essentially analogous to blood plasma or serum, the liquid substance of blood. The components of wound fluids depend on the nature of the wound. However, in acute wounds various matrix metaloproteinases (MMPs) that can degrade components of extracellular matrix including collagenases, gelatinases, and stromolysins are present. These are held in balance with various inhibitors of MMPs (TIMPs). In addition, growth and other factors are present that influence cells within the wound such as TNF-α and IL-1. These factors my have a profound effect on the persistence of a wound healing product placed into the wound environment. Many products currently available for wound healing applications heal by secondary intent, that is, by an indirect means. These applications when placed into the wound environment largely dissolve thereby releasing cells and growth factors that participate in or accelerate the intrinsic wound healing process. The object of the current invention is to heal by primary intent, that is, by direct means of providing wound closure.

Incubation of test objects in acute wound emulation fluid provides an experimental surrogate for illustrating this.

ICX-SKN, the product of this invention (a construct matured in Total Medium for 49 days with changes of medium every 2-3 days) and ICX-PRO (a composition of HDFs embedded in human fibrin and matured in control medium for a maximum of 24 hours is a product designed to heal by secondary intent by stimulating wound healing (Ref: WO 2005/000523)) were both placed into human serum (Sigma Corp.) for up to 72 days with changes of serum every 2-5 days.

The results show that ICX-PRO when placed into the wound emulation environment was found to breakdown, releasing the cells and factors that participate in wound healing within 8 days of incubation. In contrast the product of the current invention placed into the wound emulation environment persisted beyond 8 days and was maintained even after 72 days. It is important in the comparison by wound emulation to note that both ICX-PRO and the object of the current invention were originally cast from HDFs embedded in fibrin; the object of the invention was matured in Total Medium for up to 49 days prior to incubation in wound emulation fluid whereas ICX-PRO was not extensively matured beyond 24 hours in control medium. In contrast to the object of the invention, the collagen content of ICX-PRO is negligible being composed almost entirely of fibrin. Furthermore, the cells in both objects were identical at time of casting however in the case of ICX-PRO these cells, and the fluid in which they were bathed, participated in breaking down the fibrin matrix whereas they did not digest the matrix in the object of the invention.

Effects of feeding on maturation of constructs. Constructs of the present invention composed of HDFs cast originally in fibrin were fed in Total Medium with medium changed 1 time per week (one medium replacement in 7 days), 2 times per week (medium replaced every 4±1 days), or 3 times per week (medium replaced every 2±1 days) over as much as 49 days. On gross examination, those constructs subjected to relatively more frequent medium changes gained more structure seen as a "rim" of more rigid material around the circumference. The increased opacity of these constructs relative to constructs fed 1 or 2 times per week, which remained transparent and gel-like, was also indicative of increased collagen content and structure in constructs fed 3 times per week.

Currently the feeding regime is 3 times a week, although 7 changes a week (or a completely enclosed continuous flow system) may lead to improved high levels of collagen and structural integrity.

Gene expression in constructs changes with maturation. Gene expression is indicative of intrinsic and extrinsic factors that influence cells such as media conditions and states of growth and synthesis. Expression of Collagen IIIa1 and collagen Ia1 was assessed from cells obtained from constructs originally cast in fibrin as described and maintained in Total Medium for 7 days, 14 days, or 49 days (the objects of the invention), with medium changes every 2-3 days, or from cells obtained from ICX-PRO maintained in storage medium. Whereas expression of collagen Ia1 was not influenced by the feeding medium, age or matrix composition, expression of collagen IIIa1 was diminished in constructs of the invention. Although expression of this gene was noted at the early timepoints (7 and 14 days) at the latest timepoint (49 days) the expression of this gene was not detected. It is well established that collagen III is expressed early in wound healing when fibrin is prevalent in the wound environment and diminishes during later stages of wound healing. These data point to the cells present in the object of our invention are distinct from other wound healing applications as they are within a fully mature, auto-synthesised matrix and thus lack the early markers of wound healing.

In similar related experiments, constructs were fed with Total Medium once, twice or three times per week for 49 days and cells from each of these constructs were analysed for expression of genes associated with wound healing, for example collagen IIIA1 and elastin. Expression of collagen IIIA1 and elastin differed in constructs grown for the same length of time but fed 3 times, 2 times, or 1 time per week in Total Medium. Although all constructs expressed identical levels of these two genes at early timepoints (eg. at 7 days), the expression of collagen IIIA1 and elastin diminished in those constructs fed more frequently (3 times per week, the objects of the invention) relative to constructs fed less frequently (1 or 2 times per week). These data support the conjecture that constructs fed three times per week for 49 days the objects of the invention, were more mature and distinct from constructs fed less frequently (1 or 2 times per week) in not expressing genes associated with wound healing. Expression of the control or house-keeping gene GAPDH which is not influenced by growth conditions and which is not associated with wound healing was identical under all conditions.

In further experiments, HDFs grown as monolayers or embedded in fibrin and fed in Total Medium for 21 days were collected and analysed for expression of several genes. Expression of genes associated with wound healing such as elastin, collagen IA1, and collagen IIIA1, differed in HDFs incubated under the same conditions but embedded in fibrin or grown as monolayers. At this midway point in the process of maturation of the constructs (the objects of the invention), the HDFs originally embedded in fibrin, continued to synthesise gene products associated with wound healing whereas the same cells grown as a monolayer had down-regulated these genes to a large extent. However, in contrast to fully mature constructs of the invention (49 days, 3 medium changes per week) which also down-regulated elastin and collagen IIIA1, cells maintained in monolayer for 21 days had none of the structural features of a construct of the invention.

Collagen in constructs matured in Total Medium. HDFs were cast into fibrin and maintained for 49 days in control medium or Total Medium as described. Constructs of both types were frozen and fixed then sections cut and treated with either mouse antibody directed against human collagen type I or, as a control, mock-treated. A secondary FITC-conjugated antibody directed against mouse immunoglobulins was then applied to all sections. Examination of all sections under fluorescent microscopy revealed that sections stained only with second antibody and sections taken from constructs maintained in control medium displayed a similar background level of fluorescent staining. However, specific fluorescence due to reactivity of the relevant antibody with collagen I accumulated to a significant extent only in constructs maintained in Total is Medium relative to constructs maintained in control medium.

Elastin in constructs matured in Total Medium. Constructs were maintained in Total Medium for up to 49 days with medium changed every 2-3 days. The expression of elastin was analysed both in matured construct and in media collected from the matured construct. The Western blotting method using rabbit anti-human elastin (1:200) and anti-rabbit HRP (1:2000) antibodies was employed to detect the presence of elastin. Low molecular weight soluble elastin (tropoelastin ca. 60-64 Kd) was detected in the media samples. However, high molecular weight insoluble elastin was detected only in samples from constructs fed with Total medium relative to constructs fed with control medium. These data suggest that Total Medium influences the incorporation of elastin into the constructs in a high molecular weight insoluble form as it is found in dernis.

FIG. 10. Birefringence of collagen. The use of polarised light in microscopy has useful diagnostic applications due to the ability of numerous fibrous structures and proteins (as well as other molecules and crystals) to exhibit birefringence. Birefringence, or double refraction, is the decomposition of a ray of light into two rays (the ordinary ray and the extraordinary ray) when it passes through certain types of material, depending on the polarisation of the light. In microscopy, the image of a birefringent substance rotated between two crossed polarisers appears and disappears through 45° of rotation. Birefringence is the splitting of polarised light as it passes through certain materials. The light passes through a polarizer followed by the specimen of interest. It then passes through an analyzer placed at right angles to the first. The resulting light rays are within the same plane but at different wavelengths, resulting in a range of colours being displayed. On rotation of the specimen, colours are intensified or muted until black. Black areas appear as the components of the specimen become perpendicular with either polarizer or analyser. If maximum brightness/intensity is taken to be 0°, 90° shows a return to this level. Maximum darkness (extinction) occurs at 45°.

Bundles of collagen fibers are strongly birefringent. The properties of birefringence for the analysis of collagen enable the determination of fiber alignment as well as a qualitative measure of the proportion of fibers within the specimen. Whilst many biological materials are birefringent, each is differentiated by the interference pattern it produces.

The figure illustrates (A) a construct matured to 49 days in Total Medium, which was replaced every 2-3 days. Fibers are clearly visible throughout rotation, and at maximum intensity the fibers appear red, green and white. From this, it is concluded that there is no significant fibrin content but a greater content of collagen. When compared to a construct composed entirely of fibrin (B) under the same angle of polarised light at maximum intensity there is no fibrillar structure, and the construct is white only where it can be detected. Whilst fibrin is birefringent, it is far less so than collagen. The construct in (A) is strongly birefringent demonstrating the degree of fibrillar maturation of the collagen within this construct and the relative absence of fibrin.

FIG. 11. Collagen content increases with time and maturation conditions. Constructs were maintained in Control medium or in Total Medium for up to 49 days with medium changed every 2-3 days. Gross examination of constructs on days 7, 35, or 49 illustrated that the presence of growth factors such as TGF-β and EGF in Total Medium, which are absent from the control medium, contributed to significant changes in the appearance of constructs matured in this medium compared to control medium. Functionally, the constructs matured in Total Medium were more robust with greater tensile strength upon manipulation than constructs matured in control medium for the same length of time. Whereas constructs kept in control medium retained a transparent jelly-like consistency, constructs incubated throughout in Total Medium developed marked opacity relative to constructs matured in control medium and is an indication of the increased collagen content of these constructs.

In addition, in preliminary experiments the ultimate tensile strength (or breaking strength) of several types of construct was tested. Constructs were maintained in Control medium or in Total Medium for up to 49 days with medium changed every 2-3 days. In addition, control artificial test gels formed without cells purely of collagen (1 mg/ml) or fibrin (5 mg/ml) were made in the laboratory for comparison to constructs maintained as described. The graph illustrates the relative tensile strength of each of these constructs. It is evident that a synthetic collagen gel (i.e. a gel synthesised in laboratory rather than autosynthesised by cells) did not attain the tensile strength of a construct in which collagen was autosynthesised by cells within the construct. Likewise, a gel composed purely of fibrin did not attain robust tensile strength. The two matured constructs, one maintained in control medium and the other in Total Medium, displayed increased tensile strength relative to the artificial test gels. Of the two fully mature constructs it is evident that the construct matured in Total Medium attained a greater tensile strength than the construct matured in Control Medium (MPM).

The invention claimed is:

1. A method of preparing a connective tissue equivalent comprising:
   (i) casting a support matrix comprising fibrin and viable collagen-producing human dermal fibroblasts onto a support material;
   (ii) incubating in situ said support matrix in a collagen-inducing medium thereby:
      (a) inducing or enhancing collagen production by said cells to form a collagenous construct, and
      (b) degrading said fibrin;
   (iii) freeze-drying said collagenous construct; and
   (iv) re-populating said freeze-dried construct with collagen-producing cells, epithelial cells, endothelial cells, or mesenchymal cells, or mixtures thereof.

2. The method of claim 1 wherein the support matrix is incubated for 21 to 63 days.

3. The method of claim 2, wherein the collagen-inducing medium comprises phenytoin, ascorbic acid, valproic acid, cyclosporin A, nifedipine, diltiazem, verapamil HCl or amoll-dipine.

4. The method of claim 3, wherein the collagen-inducing medium further comprises Dulbecco's Modified Eagle's Medium (DMEM), Hams F-12 medium, newborn calf serum, fetal calf serum, L-glutamine, epidermal growth factor (EGF), hydrocortisone, ethanolamine, o-phosphoryl-ethanolamine, transferrin, triiodothyronine, selenium, L-proline, or glycine.

5. The method of claim 4, in which the collagen-inducing medium further comprises insulin, TGF-β, polyethylene glycol (PEG), platelet-derived growth factor (PDGF), or plasmin.

6. The method of claim 1, wherein the collagen-inducing medium comprises Dulbecco's Modified Eagle's Medium (DMEM), Hams F-12 medium, new born calf serum or fetal calf serum, L-glutamine, epidermal growth factor (EGF), hydrocortisone, ethanolamine, o-phosphoryl-ethanolamine, transferrin, triiodothyronine, selenium, L-proline, and glycine.

7. The method of claim 1, in which the collagen-inducing medium is changed daily or at least 3 times per week.

8. The method of claim 1, wherein the collagen-producing cells are incubated in a proliferating medium before incubation of the support matrix.

9. The method according to claim 8, wherein the proliferating medium comprises Dulbecco's Modified Eagle's Medium (DMEM) and newborn calf serum or fetal calf serum.

10. The method of claim 9, wherein the proliferating medium further comprises L-glutamine.

11. The method of claim 9, wherein the collagen-producing cells are incubated in the proliferating medium for a period of 0 to 21 days.

12. The method of claim 1, further comprising culturing the collagen-producing cells in a serum-free medium before or during incubation in or on the support matrix.

13. The method of to claim 12, in which the collagen-producing cells are cultured in the serum-free medium for a period of 0 to 21 days.

14. The method of claim 1, wherein the support material is a freeze-dried construct.

15. The method of claim 1, wherein the connective tissue equivalent is formed using two or more stacked freeze-dried constructs.

16. The method of claim 15, wherein at least two of the two or more freeze-dried constructs are separated by an interlaying substance.

17. The method of claim 16, wherein the interlaying substance comprises fibrin.

* * * * *